US008043851B2

(12) United States Patent
Abe et al.

(10) Patent No.: US 8,043,851 B2
(45) Date of Patent: *Oct. 25, 2011

(54) DNA ENCODING A NEOCULIN ACIDIC SUBUNIT OF CURCULIN

(75) Inventors: Keiko Abe, Warabi (JP); Tomiko Asakura, Tokyo (JP); Hiroyuki Sorimachi, Tokyo (JP); Tazuko Uenoyama, Moriyama (JP); Kenichiro Nakajima, Saitama (JP); Katsuhiko Kitamoto, Tokyo (JP); Junichi Maruyama, Tokyo (JP); Mikiya Kishi, Obu (JP)

(73) Assignee: Mitsukan Group Corporation, Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/896,676

(22) Filed: Oct. 1, 2010

(65) Prior Publication Data

US 2011/0020926 A1    Jan. 27, 2011

Related U.S. Application Data

(62) Division of application No. 10/587,539, filed as application No. PCT/JP2005/001068 on Jan. 27, 2005, now abandoned.

(30) Foreign Application Priority Data

Jan. 28, 2004  (JP) ................................ 2004-019251

(51) Int. Cl.
*C12N 15/00* (2006.01)
*C07H 21/02* (2006.01)

(52) U.S. Cl. ................... 435/320.1; 536/23.1; 536/23.6
(58) Field of Classification Search ...................... None
See application file for complete search history.

(56) References Cited

U.S. PATENT DOCUMENTS

| 5,395,921 | A   | 3/1995 | Kurihara et al. |
| 5,480,795 | A * | 1/1996 | Kurihara et al. ............ 435/91.4 |
| 5,932,438 | A * | 8/1999 | Uriach-Marsal et al. .... 435/69.1 |
| 6,090,607 | A * | 7/2000 | Van Den Broek et al. .... 435/223 |

FOREIGN PATENT DOCUMENTS

| JP | 3-190899  | 8/1991 |
| JP | 6-189771  | 7/1994 |
| JP | 10-215884 | 8/1998 |

OTHER PUBLICATIONS

Supplementary European Search Report dated Jul. 3, 2007, for Application No. EP 05 70 4174.
A. Barre, et al. "Curculin, a sweet-tasting and taste-modifying protein, is a non-functional mannose-binding lectin", *Plant Molecular Biology*, vol. 33, pp. 691-698, 1997.
Shimizu-Ibuka, et al., "Crystal Structure of Neoculin: Insights into its Sweetness and Taste-modifying Activity", *Journal of Molecular Biology*, 359:148-158, 2006.

* cited by examiner

*Primary Examiner* — David J Steadman
(74) *Attorney, Agent, or Firm* — Antonelli, Terry, Stout & Kraus, LLP.

(57) ABSTRACT

Disclosed is a polypeptide shown in the following in (A), and a protein dimer neoculin comprising the polypeptide Neoculin Acidic Subunit (NAS) and the polypeptide Neoculin Basic Subunit (NBS) and having a taste-modifying activity:
(A) a polypeptide comprising an amino acid sequence shown in SEQ ID NO.2 in the sequence listing.

4 Claims, 10 Drawing Sheets

```
DSVLL  SGQTL  YAGHS  LTSGS  YTLTI  QNNCN  LVKYQ  HGRQI
    |—C6—|—C4—|         |——C9——|—C8—|
|—D3—|                       |——C9——|
|——————————————N——————————————|
                                              |—T1—|
WASDT  DGQGS  QCRLT  LRSDG  NL IIY  DDNNM  VVWGS  DCWGN
    |—C2—|              |——C10——|           |
         |—D2—|    |——C11——|         |—C5—|
              |—D2—|    |—D4—|—D1—|
|—T4—|        |—T3—|
NGTYA  LVLQQ  DGLFV  IYGPV  LWPLG  LNGCR  SLN
|—C1—|—C12—|—C7—|—C13—|—C3—|◄
                  |——C14——|
                                         |—T2—|
```

DNA ENCODING A NEOCULIN ACIDIC SUBUNIT OF CURCULIN

This application is a Divisional application of prior application Ser. No.10/587,539, filed Jul. 28, 2006, now abandoned which is a National Stage Application, filed under 35 USC 371, of International (PCT) Application No. PCT/JP2005/001068, filed Jan. 27, 2005. The contents of Ser. No.10/587,539 are incorporated herein by reference in their entirety.

TECHNICAL FIELD

The present invention relates to a novel taste-modifying polypeptide NAS, the DNA thereof and the use thereof. More specifically, the invention relates to the polypeptide NAS, the gene thereof, the dimeric protein neoculin containing the polypeptide and having a taste-modifying activity, and a taste-modifying composition containing neoculin.

BACKGROUND OF THE INVENTION

*Curculigo latifolia* is a plant spontaneously growing in west Malaysia and a southern part of Thailand, which is classified into Liliaceae. It is said that the curculin isoform (referred to as curculin hereinafter) contained in the plant is useful as a taste-modifying substance giving sweet taste when the isoform is eaten before drinking water or eating a sour substance.

Conventionally known subunits constituting curculin include for example curculin A and curculin B.

The entire amino acid sequence of curculin A has been determined (see for example patent literature 1). The entire amino acid sequence of curculin B and the nucleotide sequence thereof are disclosed. It is verified that curculin B is different in the amino acid composition from curculin A in terms of several amino acids (see for example patent literature 2).

It has been understood that these subunits both constitute curculin in a form of homodimer and have a taste-modifying function. However, the taste-modifying functions thereof are not sufficient enough to be added into foods.

In accordance with the invention, however, it was succeeded to identify a novel dimeric protein with a heterodimer structure comprising two subunits having different amino acid sequences, namely NAS and NBS. The protein is designated as neoculin. The results are disclosed (see non-patent literature 1). It is first identified in the invention that neoculin has a taste-modifying function sufficient enough for addition into foods.

So as to enable the highly efficient production of neoculin, the results of the expression of the genes encoding the subunits with two different amino acid sequences, namely NAS and NBS, in a prokaryote *Escherichia coli* are disclosed (see for example non-patent literature 2).

Possibly due to the generation of NAS and NBS in the form of inclusion body in the bacterial cell of *Escherichia coli*, an accurate heterodimer of NAS and NBS with the exertion ability of the taste-modifying activity can scarcely be generated via the simple expression in *Escherichia coli*.

So as to exert the taste-modifying function, then, procedures have been required, including recovery of the inclusion body, solubilization thereof using a solubilizing agent solution such as guanidine chloride, and reconstitution. The requirement of the use of such reagent is disadvantageous in terms of laborious works and production cost. Additionally, such use of the reagent is not suitable for industrial production from the standpoint of safety profile when the produced neoculin is used for foods.

In such circumstances, it has been desired to screen for a substance with higher practical applicability and a better taste-modifying function and to develop a safe and efficient production method applicable to foods Patent literature 1: JP-A-Hei 3-190899
Patent literature 2: JP-A-Hei 6-189771
Non-patent literature 1: "Biosci. Biotechnol. Biochem.", Vol. 68, No.6, p. 1403-1407, 2004
Non-patent literature 2: "FEES Letters", Vol. 573, p 135-138, 2004

DISCLOSURE OF THE INVENTION

Problems that the Invention is to Solve

As described above, it is an object of the invention to find a substance with a better taste-modifying function and determine the structure of the taste-modifying substance, as well as to elucidate the structure thereof at a gene level and determine the primary structure of the substance and obtain the gene encoding the substance. Additionally, it is an object of the invention to provide a novel taste-modifying composition characteristically containing the taste-modifying substance.

Means for Solving the Problems

The inventors have made investigations so as to solve the problems. Thus, the inventors have successfully found a novel dimeric protein with a heterodimer structure different from that of curculin, in a fruit extract from *Curculigo latifolia*, which has an excellent taste-modifying activity. Thus, the inventors have designated the protein neoculin.

The inventors have, found neoculin greatly reduces the sourness, bitterness or astringency of foods and drinks and additionally that neoculin has an activity to enhance the taste of foods and drinks, namely a taste-modifying activity. The inventors have found that neoculin has a far better taste-modifying action than that of curculin and is highly practically applicable.

In other words, the inventors have focused their attention to the fact that neoculin is a heterodimer of a novel subunit NAS (neoculin acidic subunit) never having been known and a subunit NBS (neoculin basic subunit) such as curculin A or B having been known as subunits of curculin, in the course of purifying neoculin and determining the structure thereof.

The inventors have carried out the structural analysis of the novel subunit NAS. Compared with the homology between the known curculin A and B constituting NBS, a novel polypeptide with a lower homology has been obtained.

The inventors therefore have analyzed the DNA of the gene encoding the polypeptide NAS to elucidate neoculin at the gene level. The inventors have found, besides the nucleotide sequence of the mature form of the protein NAS, the nucleotide sequence of a precursor protein (PNAS) containing a signal peptide and an extension peptide.

The inventors have verified that neoculin has a taste-modifying activity when added actually to foods and drinks.

Furthermore, the inventors have made investigations about an expression system of neoculin in other species. Consequently, the inventors have established an expression system which allows the genes encoding NAS or PNAS and NBS to express in a host and allows neoculin to be secreted and generated out of the bacterial cell as a heterodimer having taste-modifying function.

The invention has been based on the findings described above.

The invention includes a polypeptide NAS shown below in (A) or (B):
(A) a polypeptide comprising an amino acid sequence shown in SEQ ID NO.2 in the sequence listing;
(B) a polypeptide comprising an amino acid sequence with the substitution, deletion, insertion, addition or inversion of one or several amino acids in the amino acid sequence shown in SEQ ID NO.2 in the sequence listing, which polypeptide can form the neoculin dimer having a taste-modifying activity together with a polypeptide NBS shown below in (a) or (b):
(a) a polypeptide comprising an amino acid sequence shown in SEQ ID NO.6 in the sequence listing;
(b) a polypeptide comprising an amino acid sequence with the substitution, deletion, insertion, addition or inversion of one or several amino acids in the amino acid sequence shown in SEQ ID NO.6 in the sequence listing, which polypeptide can be a subunit constituting curculin.

The invention includes the polypeptide NAS, which is glycosylated with an N-linked sugar chain comprising mannose/N-acetylglucosamine/fucose/xylose at a ratio of 3/2/1/1.

The invention includes DNA of a gene encoding the polypeptide NAS shown below in (A) or (B):
(A) a polypeptide comprising an amino acid sequence shown in SEQ ID NO.2 in the sequence listing;
(B) a polypeptide comprising an amino acid sequence with the substitution, deletion, insertion, addition or inversion of one or several amino acids in the amino acid sequence shown in SEQ ID NO.2 in the sequence listing, which polypeptide can form the neoculin dimer having a taste-modifying activity together with the polypeptide NBS shown above in (a) or (b).

The invention includes a DNA shown below in (A) or (B):
(A) DNA containing the nucleotide sequence comprising the nucleotides 70 to 408 in the nucleotide sequence shown in SEQ ID NO.1 in the sequence listing;
(B) DNA hybridizing with the DNA of the nucleotide sequence comprising the nucleotides 70 to 408 in the nucleotide sequence shown in SEQ ID NO.1 in the sequence listing or with the DNA of a nucleotide sequence capable of functioning as a probe prepared from at least a part of the nucleotide sequence under stringent conditions and encoding a polypeptide capable of forming the neoculin dimer having a taste-modifying activity together with the polypeptide NBS shown above in (a) or (b).

The invention includes a polypeptide PNAS shown below in (A) or (B):
(A) a polypeptide comprising an amino acid sequence shown in SEQ ID NO.3 in the sequence listing;
(B) a polypeptide comprising an amino acid sequence with the substitution, deletion, insertion, addition or inversion of one or several amino acids in the amino acid sequence shown in SEQ ID NO.3 in the sequence listing, which polypeptide grows to the mature polypeptide NAS via processing and so as to be able to form the neoculin dimer having a taste-modifying activity together with the polypeptide NBS shown above in (a) or (b).

The invention includes the polypeptide PNAS, which is glycosylated with an N-linked sugar chain comprising mannose/N-acetylglucosamine/fucose/xylose at a ratio of 3/2/1/1.

The invention includes DNA of a gene encoding the polypeptide PNAS shown below in (A) or (B):
(A) a polypeptide comprising an amino acid sequence shown in SEQ ID NO.3 in the sequence listing;
(B) a polypeptide comprising an amino acid sequence with the substitution, deletion, insertion, addition or inversion of one or several amino acids in the amino acid sequence shown in SEQ ID NO.3 in the sequence listing, which polypeptide grows to the mature polypeptide NAS via processing and so as to be able to form the neoculin dimer having a taste-modifying activity together with the polypeptide NBS shown above in (a) or (b).

The invention includes, which is the DNA shown below in (A) or (B):
(A) DNA containing a nucleotide sequence comprising the nucleotides 4 to 477 in the nucleotide sequence shown in SEQ ID NO.1 in the sequence listing;
(B) DNA hybridizing with the DNA of the nucleotide sequence comprising: the nucleotides 4 to 477 in the nucleotide sequence shown in SEQ ID NO.1 in the sequence listing or with the DNA of a nucleotide sequence capable of functioning as a probe prepared from at least a part of the nucleotide sequence under stringent conditions and encoding a polypeptide growing to the mature polypeptide NAS via processing so as to be able to form the neoculin dimer having a taste-modifying activity together with the polypeptide NBS shown above in (a) or (b).

The invention includes a dimeric protein neoculin comprising the polypeptide NAS and the polypeptide NBS shown above in (a) or (b) and having a taste-modifying activity.

The invention includes a taste-modifying composition containing the dimeric protein neoculin as the active ingredient.

The invention includes a recombinant vector carrying a nucleotide sequence constituting the DNA above.

The invention includes a recombinant vector carrying a nucleotide sequence constituting the DNA of the gene encoding the polypeptide NBS shown below in (a) or (b):
(a) a polypeptide comprising an amino acid sequence shown in SEQ ID NO.6 in the sequence listing;
(b) a polypeptide comprising an amino acid sequence with the substitution, deletion, insertion, addition or inversion of one or several amino acids in the amino acid sequence shown in SEQ ID NO.6 in the sequence listing, which polypeptide can be a subunit constituting curculin.

The invention includes the recombinant vector, which is a vector functioning in eukaryotic organisms.

The invention includes the recombinant vector, which is a vector functioning in filamentous fungi.

The invention includes the recombinant vector, which is a vector functioning in koji molds.

The invention includes a transformant carrying the recombinant vectors.

The invention includes a method for producing neoculin, including a step of culturing the transformant.

Effect of the Invention

In accordance with the invention, a novel dimeric protein neoculin with an excellent taste-modifying activity and in a heterodimer structure different from that of curculin is provided. Using the protein, a novel taste-modifying composition practically applicable to foods and the like is provided.

In accordance with the invention, further, the amino acid sequence of a subunit constituting the protein is provided. Thus, the protein can be provided by an appropriate synthetic method following the amino acid sequence.

In accordance with the invention, the DNA of the gene encoding the protein is provided. Selecting appropriate hosts, specifically koji molds, and using genetic engineering, technology, the protein can be provided efficiently.

DESCRIPTION OF SYMBOLS

Figures 7, 8:
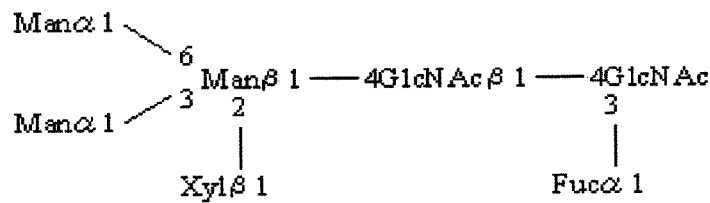
FIG. 7 depicts the amino acid sequence of NAS (SEQ ID NO: 2).
FIG. 8 depicts a sugar chain structure speculated from the analysis of the sugar composition of the sugar chain of NAS.

In FIG. 7, N in the line 4 shows an amino acid sequence part determined from the N terminus; C1-14 show amino acid sequences of peptides obtained via chymotrypsin digestion; D1-4 show amino acid sequences of peptides obtained via digestion with endoproteinase Asp-N; and T1-4 show amino acid sequences of peptides obtained via trypsin digestion. Additionally, ← shows an amino acid sequence determined from the C terminus.

BEST MODE FOR CARRYING OUT THE INVENTION (1) Dimeric Protein Neoculin of the Invention The neoculin of the invention is a dimeric protein comprising the polypeptide NAS and the polypeptide NBS shown below in (a) or (b) and having a taste-modifying activity.

(a) A polypeptide comprising an amino acid sequence shown in SEQ ID NO.6 in the sequence listing.

(b) A polypeptide comprising an amino acid sequence with the substitution, deletion, insertion, addition or inversion of one or several amino acids in the amino acid sequence shown in SEQ ID NO.6 in the sequence listing, which polypeptide can be a subunit constituting curculin.

As described below in (2), the polypeptide NAS (neoculin acidic subunit) is a protein first reported by the inventors. Additionally, the polypeptide NBS (neoculin basic subunit) means a polypeptide shown in (a) or (b). As described below in (2), specifically, the polypeptide NBS means known curculin subunits such as curculin A and curculin B.

Both the polypeptides form a stable heterodimer via the binding between NAS with a sugar chain and NBS without any sugar chain.

The neoculin of the invention can be obtained, for example, from *Curculigo latifolia* as a plant belonging to Liliaceae by an appropriate combination of known isolation and purification methods.

As described in Example 1(1), for example, a freeze-dried fruit of *Curculigo latifolia* is homogenized to generate a powder, which is extracted in a large volume of pure water. Via centrifugation, the resulting supernatant is discarded, to remove unnecessary materials. The remaining precipitate is extracted in an aqueous acidic solution of pH 2.0 or less, to obtain neoculin in the extract solution. Subsequently, the extract solution is neutralized, concentrated, desalted and dried by general processing methods (preferably, a method without heating), to obtain the protein neoculin sufficient enough for practical application.

The polypeptide NAS described below in (2) is artificially prepared, and then, the polypeptide NBS obtained either by extraction and purification from neoculin or known curculin or by artificial synthesis is bound to the resulting NAS, to obtain neoculin. Further, neoculin can be obtained by the production method described below in (6).

The neoculin of the invention has a taste-modifying activity. Herein, the phrase taste-modifying activity means an activity prominently reducing sourness, bitterness or astringency as well as enhancing the taste of foods or drinks. Specifically, the activity means an activity suppressing the bitterness of bitter foods or drinks, an activity suppressing the astringency of foods or drinks with astringent taste, an activity giving sweetness to foods or drinks, an activity giving sweetness to sour foods or drinks and an activity suppressing the sourness of sour foods or drinks.

(2) Polypeptide NAS of the Invention

The polypeptide NAS of the invention is a polypeptide shown below in (A) or (B).

(A) A polypeptide comprising an amino acid sequence shown in SEQ ID NO.2 in the sequence listing.

(B) A polypeptide comprising an amino acid sequence with the substitution, deletion, insertion, addition or inversion of one or several amino acids in the amino acid sequence shown in SEQ ID NO.2 in the sequence listing, which polypeptide can form the neoculin dimer having a taste-modifying activity together with the polypeptide NBS shown below in (a) or (b).

(a) A polypeptide comprising an amino acid sequence shown in SEQ ID NO.6 in the sequence listing;
(b) A polypeptide comprising an amino acid sequence with the substitution, deletion, insertion, addition or inversion of one or several amino acids in the amino acid sequence shown in SEQ ID NO.6 in the sequence listing, which polypeptide can be a subunit constituting curculin.

(A) a polypeptide comprising the amino acid sequence shown in SEQ ID NO.2 in the sequence listing is a subunit first identified by the inventors as one of subunits constituting the neoculin dimer having a taste-modifying activity, together with the polypeptide NBS.

As described above, the polypeptide NBS (neoculin basic subunit) means (a) a polypeptide comprising an amino acid sequence shown in SEQ ID NO.6 in the sequence listing, or (b) a polypeptide comprising an amino acid sequence with the substitution, deletion, insertion, addition or inversion of one or several, preferably one to 5 amino acids in the amino acid sequence shown in SEQ ID NO.6 in the sequence listing, which polypeptide can be a subunit constituting curculin. Such polypeptide NBS specifically includes the polypeptide comprising an amino acid sequence shown in SEQ ID NO.6 in the sequence listing (curculin B), a polypeptide obtained by substituting tryptophan-73 in the amino acid sequence with asparagine (referred to as curculin B'), and a polypeptide obtained by substituting lysine-28, tryptophan-73, tryptophan-78 and asparagine-81 with asparagine, asparagine, cysteine and alanine, respectively (curculin A).

Thus, the polypeptide NAS of the invention may be (A) a polypeptide comprising an amino acid sequence shown in SEQ ID NO.2 in the sequence listing and may be a polypeptide substantially identical to the polypeptide (A), namely (B) a polypeptide comprising an amino acid sequence with the substitution, deletion, insertion, addition or inversion of one or several, preferably one to 5 amino acids in the amino acid sequence shown in SEQ ID NO.2 in the sequence listing and being capable of forming the neoculin dimer having a taste-modifying activity together with the polypeptide NBS.

The polypeptide NAS is preferably glycosylated with a sugar chain, particularly preferably an N-linked sugar chain because the polypeptide NAS can get an increased binding to the polypeptide NBS so that the polypeptide NAS can form neoculin with a higher stability. Herein, the N-linked sugar chain means the general name of a sugar chain structure extending from N-acetylglucosamine, as the start point, bound to the asparagine residue existing in the primary structure of protein.

Among the N-linked sugar chains, an N-linked sugar chain comprising mannose/N-acetylglucosamine/fucose/xylose at a ratio of 3/2/1/1 is preferable. Specifically, the N-linked sugar chain is preferably a sugar chain in the structure shown in FIG. 8. Furthermore, a part of the structure shown in FIG. 8 may have addition, deletion, substitution or modification.

From the standpoint of the binding feature of such N-linked sugar chain, the binding site of the N-linked sugar chain in the polypeptide NAS may possibly be asparagine-81 in the amino acid sequence shown in SEQ ID NO.2 in the sequence listing.

The polypeptide NAS of the invention is a subunit forming neoculin and can be obtained from a fruit of *Curculigo latifolia* containing neoculin by a combination of known isolation and purification methods. As described in Example 1 (2) and (3), neoculin, obtained by the method described in Example 1 (1) is purified by an appropriate combination of known ion exchange chromatographic methods. As described in Example 2, then, the purified product is applied to a cation exchange column by general methods, so that the polypeptide NBS with an isoelectric point of 8.6 is adsorbed onto the column while the polypeptide NAS is obtained in a non-adsorbed fraction. The non-adsorbed fraction is applied to an anion exchange column by general methods, so that the polypeptide NAS with an isoelectric point of 4.7 is adsorbed onto the column. Thus, the NAS is eluted, desalted and dried.

The polypeptide NAS may also, be obtained by genetic engineering methods based on the DNA shown below in (4).

The polypeptide shown above in (A) or (B) can be produced by appropriate synthetic methods, for example solid phase synthetic method, partial solid phase synthetic method and solution synthetic method as well as chemical synthetic methods such as fluorenylmethyloxycarbonyl method (Fmoc method), and t-butyloxycarbonyl method (tBOC method). Additionally, the polypeptide shown in (B) may be obtained by a site-directed mutagenesis including altering the amino acid sequence shown in SEQ ID NO.2 in the sequence listing into an amino acid sequence such that one or several, preferably one to 5 amino acids may be substituted, deleted, inserted, added or inverted.

(3) Polypeptide PNAS of the Invention

The polypeptide PNAS of the invention is a polypeptide shown below in (A) or (B).
(A) A polypeptide comprising an amino acid sequence shown in SEQ ID NO.3 in the sequence listing;
(B) A polypeptide comprising an amino acid sequence with the substitution, deletion, insertion, addition or inversion of one or several amino acids in the amino acid sequence shown in SEQ ID NO.3 in the sequence listing, which polypeptide grows to the mature polypeptide NAS via processing so as to be able to form the neoculin dimer having a taste-modifying activity together with the polypeptide NBS shown above in (a) or (b).

Herein, (A) a polypeptide comprising an amino acid sequence shown in SEQ ID NO.3 in the sequence listing is first identified by the inventors as a polypeptide NAS precursor containing the signal peptide and extension peptide of the polypeptide NAS described above in (2). Specifically, (A) a polypeptide comprising an amino acid sequence shown in SEQ ID NO.3 in the sequence listing is generated as a precursor of the polypeptide comprising an amino acid sequence shown in SEQ ID NO.2 in the sequence listing in the cells of the plant and is then processed into (A) a polypeptide comprising an amino acid sequence shown in SEQ ID NO.2 in the sequence listing.

Thus, the polypeptide PNAS as an NAS precursor may be (A) a polypeptide comprising an amino acid sequence shown in SEQ ID NO.3 in the sequence listing but may be a polypeptide substantially identical to the polypeptide (A), namely (B) a polypeptide comprising an amino acid sequence with the substitution, deletion, insertion, addition or inversion of one or several, or preferably 1 to 5, amino acids in the amino acid sequence shown in SEQ ID NO.3 in the sequence listing and growing to the mature polypeptide NAS via processing and thereafter can form the neoculin dimer having a taste-modifying activity together with the polypeptide NBS.

The polypeptide NBS is as described above in (2).

The polypeptide PNAS is preferably glycosylated with a sugar chain, particularly preferably an N-linked sugar chain, because the polypeptide NAS obtained through the cleavage of the signal peptide (the part comprising the amino acids 1 to 22 in the amino acid sequence shown in SEQ ID NO.3) and the extension peptide (the part comprising the amino acids 136 to 158 in the amino acid sequence shown in SEQ ID NO.3) can get an increased binding to the polypeptide NBS via processing so that the polypeptide NAS can form neoculin with a higher stability. Among the N-linked sugar chains, an N-linked sugar chain comprising mannose/N-acetylglucosamine/fucose/xylose at a ratio of 3/2/1/1 is preferable. Specifically, the N-linked sugar chain is a sugar chain in the structure shown in FIG. 8. Furthermore, a part of the structure shown in FIG. 8 may have addition, deletion, substitution or modification.

From the standpoint of the binding feature of such N-linked sugar chain, the binding site of the N-linked sugar chain in the polypeptide PNAS may possibly be asparagine-103 in the amino acid sequence shown in SEQ ID NO.3 in the sequence listing.

The polypeptide PNAS as described above is a precursor of the subunit NAS forming neoculin and can therefore be obtained by genetic engineering methods based on the DNA of the gene encoding PNAS as shown below in (4). The polypeptide shown in above (A) or (B) can be produced by appropriate synthetic methods, for example solid phase synthetic method, partial solid phase synthetic method and solution synthetic method as well as chemical synthetic methods such as fluorenylmethyloxycarbonyl method (Fmoc method), and t-butyloxycarbonyl method (tBOC method). Additionally, the polypeptide shown in (B) may be obtained by a site-directed mutagenesis including altering the amino acid sequence shown in SEQ ID NO.2 in the sequence listing into an amino acid sequence such that the amino acid sequence may include the substitution, deletion, insertion, addition or inversion of one or several, preferably one to 5 amino acids.

(4) DNAs of the Invention

The DNAs of the invention are the DNA of the gene encoding the polypeptide NAS described above in (2) and the DNA of the gene encoding the polypeptide PNAS described above in (3). Specifically, first, the DNA of the gene encoding the polypeptide NAS is the DNA of the gene encoding the polypeptide NAS described above in (2), more specifically the polypeptide NAS described below in (A) or (B):

(A) a polypeptide comprising an amino acid sequence shown in SEQ ID NO.2 in the sequence listing;
(B) a polypeptide comprising an amino acid sequence with the substitution, deletion, insertion, addition or inversion of one or several amino acids in the amino acid sequence shown in SEQ ID NO.2 in the sequence listing, which polypeptide can form the neoculin dimer having a taste-modifying activity together with the polypeptide NBS shown above in (a) or (b).

The DNA of the gene encoding the polypeptide NAS may be obtained as (A) DNA containing a nucleotide sequence comprising the nucleotides 70 to 408 in the nucleotide sequence shown in SEQ ID NO.1 in the sequence listing, and may be obtained as DNA hybridizing with the DNA of a nucleotide sequence substantially identical to the aforementioned nucleotide sequence, namely (B) the DNA of the nucleotide sequence comprising the nucleotides 70 to 408 in the nucleotide sequence shown in SEQ ID NO.1 in the sequence listing or a nucleotide sequence capable of functioning as probe prepared from at least a part of the aforementioned nucleotide sequence, under stringent conditions and encoding a polypeptide capable of forming the neoculin dimer having a taste-modifying activity together with the polypeptide NBS. Herein, the polypeptide NBS is as described above in (2).

Herein, the phrase "stringent conditions" means conditions under which so-called specific hybrid is formed but non-specific hybrid is not formed. It is difficult to numerically express the conditions clearly. Nonetheless, one example thereof is a condition under which DNAs with high homology, for example 90% or more homology, is hybridized together, while DNAs with lower homology is never hybridized, or a rinse condition for general hybridization, for example a rinse condition of 0.1×ssc at a salt concentration corresponding to 0.1% SDS and 65° C.

Such DNA of the gene encoding the polypeptide NAS can be obtained for example by extracting mRNA from a fruit of *Curculigo latifolia* several weeks after pollination, synthetically preparing cDNA with reverse transcription•polymerase chain reaction (RT-PCR), and packaging the cDNA in a phage vector. Then, infection with the phage vector is carried out to obtain a cDNA library. Subsequently, a probe prepared on the basis of the amino acid sequence of the polypeptide NAS clarified in the invention is allowed to identify the intended DNA with a plaque hybridization, and the intended DNA is recovered.

The DNA may also be obtained by PCR using, as a primer, an oligonucleotide synthetically prepared on the basis of the nucleotide sequence comprising the nucleotides 70 to 408 in the nucleotide sequence described as SEQ ID NO.1 in the sequence listing. Otherwise, the DNA shown above in (A) or (B) may be synthetically prepared with various commercially available DNA synthesizers.

Additionally, the DNA shown in (B) may be obtained, for example, by site-directed mutagenesis including appropriately introducing mutations such as substitution, deletion, insertion or addition into the nucleotide sequence comprising the nucleotides 70 to 408 in the nucleotide sequence shown in SEQ ID NO.1 in the sequence listing. The DNA may also be obtained by known mutation processes.

Secondly, the DNA of the gene encoding the polypeptide PNAS is the DNA of the gene encoding the polypeptide PNAS described above in (3), more specifically the polypeptide PNAS shown below in (A) or (B).

(A) The polypeptide comprising an amino acid sequence shown in SEQ ID NO.3 in the sequence listing.
(B) The polypeptide comprising an amino acid sequence with the substitution, deletion, insertion, addition or inversion of one or several amino acids in the amino acid sequence shown in SEQ ID NO.3 in the sequence listing, which polypeptide grows to the mature polypeptide NAS via processing so as to be able to form the neoculin dimer having a taste-modifying activity together with the polypeptide NBS shown above in (a) or (b).

The DNA of the gene encoding such polypeptide PNAS may specifically be obtained as (A) DNA containing a nucleotide sequence comprising the nucleotides 4 to 477 in the nucleotide sequence shown in SEQ ID NO.1 in the sequence listing or as (B) DNA hybridizing with the DNA of a nucleotide sequence substantially identical to the aforementioned nucleotide sequence, namely the nucleotide sequence comprising the nucleotides 4 to 477 in the nucleotide sequence shown in SEQ ID NO.1 in the sequence listing or a nucleotide sequence capable of functioning as probe prepared from at least a part of the aforementioned nucleotide sequence, under stringent conditions and encoding a polypeptide growing to the mature polypeptide NAS via processing so as to be able to form the neoculin dimer having a taste-modifying activity together with the polypeptide NBS. As described in the above (2) is about the polypeptide NBS.

The phrase "stringent conditions" means the same as described for the DNA of the gene encoding the polypeptide NAS.

Such DNA of the gene encoding the polypeptide PNAS can be obtained, for example, in the same manner as in the case of the mature polypeptide NAS from a fruit of *Curculigo latifolia* several weeks after pollination. Additionally, the DNA shown above in (A) or (B) may also be obtained by PCR using, as a primer, an oligonucleotide synthetically prepared on the basis of the nucleotide sequence of the nucleotides 4 to 477 in the nucleotide sequence shown in SEQ ID NO:1 in the sequence listing, or may be synthesized with various commercially available DNA synthesizers.

Additionally, the DNA shown in (B) may also be obtained by site-directed mutagenesis including appropriately introducing mutations such as substitution, deletion, insertion or addition into the nucleotide sequence comprising the nucleotides 4 to 477 in the nucleotide sequence shown in SEQ ID NO.1 in the sequence listing. Additionally, the DNA may be obtained by known mutation processes.

It is needless to say that the two DNAs of the invention may satisfactorily contain a regulatory element for the nucleotide sequences and a structural genes.

(5) Taste-modifying Composition of the Invention

The taste-modifying composition of the invention characteristically contains a dimeric protein neoculin having a taste-modifying activity. Neoculin is as described above in (1).

The taste-modifying composition of the invention may be incorporated as it is but may be added at an appropriate amount to foods or drinks including vegetable juice, fruit juices of for example grapefruit, and various seasoning liquids for cooking for sushi neta (sushi topping), or pharmaceutical agents or the like. The blended amount of neoculin in this case is for example 5 to 5,000 μg/ml, particularly preferably 50 to 500 μg/ml, when the composition containing a neoculin powder highly purified is added to a drink.

Additionally, the taste-modifying composition of the invention may be used after processing into the form of powder, solution, sheet, spray, granule or emulsion, depending on the property of a food or a drink or a pharmaceutical agent as a blend subject.

(6) Method for Producing Dimeric Protein Neoculin in Accordance with the Invention In accordance with the invention, genes individually encoding NAS and NBS as two types of subunits constituting neoculin and the gene encoding PNAS are identified.

In accordance with the invention, a recombinant vector carrying the DNA of the gene encoding NAS or the DNA of the gene encoding PNAS as well as a recombinant vector carrying the DNA of the gene encoding NBS is provided for a host-vector system for highly efficiently expressing the genes to industrially produce neoculin. In accordance with the invention, further, a transformant harboring a combination of the two types of recombinant vectors is also provided. In accordance with the invention, furthermore, a method for producing a dimeric protein neoculin having a taste-modifying activity is provided, which includes culturing the transformant.

So as to produce neoculin utilizing a host-vector system in accordance with the invention, essentially, the two types of recombinant vectors in accordance with the invention, namely a recombinant vector carrying the DNA of the gene encoding NAS or the DNA of the gene encoding PNAS and a recombinant vector carrying the DNA of the gene encoding NBS are simultaneously introduced into a host.

This is because both the subunit proteins namely NAS and NBS must be generated since neoculin is a heterodimer comprising the different subunits of NAS and NBS.

Such recombinant vectors of the invention are required to have an expression and regulation functions including a promoter function so as to express the gene encoding NAS or the gene encoding NBS.

Additionally, the recombinant vectors preferably have such a function that NAS and NBS generated via the expression of the NAS gene and the NBS gene introduced into the vectors inside the host are secreted from the host cells. In addition to the genes encoding NAS and NBS, specifically, a gene encoding a protein secreted by a host, for example a gene of a secretory protein α-amylase in a koji mold in case of *Aspergillus oryzae* is integrated in an appropriate vector to express the genes for expression in a form of a fusion protein of NAS and NBS with α-amylase, NAS and NBS can be secreted and generated extracellularly from the host cells. Instead of the amylase, glucoamylase (GlaA) may also be used.

In case of the expression in the form of the fusion protein as described above, preferably, the recombinant vectors have a processing function working for altering the fusion protein into NAS or NBS alone. Specifically, for example, utilizing a nucleotide sequence encoding an amino acid sequence (Lys-Arg, Lys-Lys, Arg-Lys, Arg-Arg) recognized by a KEX2-like protease existing in the Golgi body of a koji mold, the nucleotide sequence is integrated and expressed in between the α-amylase and NAS and between the α-amylase and NBS, and the fusion gene is expressed. After the expression, KEX2-like protease digestion is carried out to isolate α-amylase from the resulting fusion protein generated by the recombinant vectors, to obtain the protein dimer of NAS and NBS.

For cleavage with KEX2 as described above, possibly, the cleavage may sometimes be inaccurate, depending on the conformation around the recognition sequence by KEX2, and the conformation around the cleavage site may be complicated as neoculin forms heterodimer. Therefore, the cleavage efficiency and the accuracy of the cleavage may preferably be improved. For example, about three residues of amino acids with lower molecular weights and smaller side chains such as Gly, Ala and Ser to hardly cause steric hindrance can be inserted immediately before Asp at the N termini of NAS and NBS.

Such a series of procedures may be done in a simpler manner utilizing a vector construction kit (Multisite Gateway Three-Fragment Vector Construction Kit; manufactured by Invitrogen). In other words, the construction is done in an order of (a) the preparation of 5' entry clone, (b) the preparation of the entry clone of an intended gene, (c) the preparation of 3' entry clone, (d) the preparation of a recombinant vector from a recombination of the three types of entry clones and destination vector, utilizing the kit, to prepare a desired recombinant vector. Based on general methods, alternatively, a necessary gene fragment is excised and then introduced into an appropriate site on a vector, to prepare a recombinant vector.

Specific examples of the recombinant vector in accordance with the invention include pgFa3GNaSJ (FIG. 10) as a recombinant vector with the gene encoding NAS as introduced therein, and pgFa3GNbTa (FIG. 11) as a recombinant vector with the NBS gene introduced therein.

In case that introduction of the gene encoding PNAS, for example, plasmids with the gene encoding PNAS in place of the gene encoding NAS in pgFa3GNaSJ or the gene encoding NBS in pgFa3GNbTa is also listed.

The transformant of the invention is now described. The transformant of the invention is prepared by integrating the two types of recombinant vectors into an appropriate host.

The host for the recombinant vector in accordance with the invention is preferably a eukaryote. Prokaryote such as *Escherichia coli* are not preferable as the hosts. Because the protein is generated as an inclusion body in the bacterial cell as described in the Section "Background Art", so as to alter the inclusion body into the accurate heterodimer capable of exerting the taste-modifying activity, therefore, the polypeptides NAS and NBS constituting the inclusion body are required to be once solubilized using a solubilization agent such as guanidine chloride and then reconstructed (reconstituted). When eukaryote such as koji mold are used as the host, in contrast, the use of reagents such as solubilization agent is not required. With no need of extra processes such as reconstruction, additionally, the protein can be secreted and generated as neoculin capable of exerting the taste-modifying activity.

The host for introducing the recombinant vector therein in accordance with the invention is preferably a filamentous fungus among eukaryote, more preferably koji mold among them. Specifically, koji mold belonging to *Aspergillus oryzae*, typically an *Aspergillus oryzae* strain NS4 is preferable.

As an example of the transformant, the inventors obtained an *Aspergillus oryzae* strain NS-NAB2 by introducing a recombinant vector of the genes encoding NAS and NBS into the *Aspergillus oryzae* strain NS4. The *Aspergillus oryzae* strain NS-NAB2 has been deposited under accession No. FERM BP-10209 at the International Patent Organism Depositary, the National Institute of Advanced Industrial Science and Technology, Chuo-6, Tsukuba-shi, Ibaraki-ken, Japan.

In accordance with the invention, the dimeric protein neoculin with the taste-modifying activity can be produced by culturing the transformant.

The transformant is preferably cultured under conditions such that the expression ratio of the gene encoding NAS and the gene encoding NBS may be a specific ratio. When either one of the expression levels is one-sided, the efficiency of the generated heterodimer comprising NAS and NBS is lower, because homodimers are also formed. Thus, the production efficiency of neoculin is then lowered.

In accordance with the invention, the ratio of the gene encoding NAS and the gene encoding NBS for use in the transformation procedure is set at 1:5. In that case, a strain with a high expression level could be screened in the resulting transformants with high efficiency. So as to achieve a high production efficiency, culturing is done preferably under a condition of a culture medium around pH 8.0.

In such manner, the recombinant vector and the transformant as well as the heterodimer with the taste-modifying activity in the invention can be produced efficiently.

Examples are now given below.

EXAMPLE 1

A fruit of *Curculigo latifolia* was purified by the following procedures to obtain the novel protein with the taste-modifying activity.

(1) Preparation of Crude Extract Solution 40 liters of pure water were added to about 1 kg of the freeze-dried fruit of *Curculigo latifolia* (freeze-dried fruit powder in Table 1) for homogenization for 15 minutes. Then, centrifugation at 6,000 rpm for 20 minutes was done to discard the supernatant (the supernatant had no taste-modifying activity). The procedure described above was repeated twice, to obtain the residual precipitate.

Then, 20 liters of 0.05N sulfuric acid were added to the residual precipitate, for homogenization for 10 minutes. Then, centrifugation at 6,000 rpm for 20 minutes was done to recover the supernatant. The procedure described above was repeated twice The resulting precipitate had no taste-modifying activity.

Then, 2 liters of 1N sodium hydroxide were added to the extract solution for neutralization, to obtain a crude extract solution (0.05N sulfate extract solution in Table 1) containing the active substance.

(2) Purification on Amberlite IRC-50 Column

About 40 liters of the crude extract solution obtained in (1) were passed through an Amberlite IRC-50 column (manufactured by Organo; a 8 cm diameter×30 cm) equilibrated with 50 mM phosphate buffer, pH 5.5 for adsorption. Continuously, the column was washed with one liter of 50 mM phosphate buffer, pH 5.5, and eluted with 1.5 liters of 50 mM phosphate buffer, pH 5.5 containing 1M sodium chloride, to obtain a fraction with a taste-modifying activity. Ammonium sulfate was added to the active fraction to 60% saturation, to separate out the active substance, which was centrifuged at 6,000 rpm for 30 minutes. The resulting precipitate was dissolved in 100 ml of 0.2N acetic acid, to recover a solution of the active substance (Amberlite IRC-50 Chromatography in Table 1).

(3) Purification on Sephadex G-25 Column 100 ml of the solution of the active substance as obtained in (2) was applied to a Sephadex G-25 column (manufactured by Amersham Biosciences; a 8 cm diameter×30 cm) equilibrated with 0.2N acetic acid, for desalting. The solution of the active substance was freeze-dried to obtain a highly purified neoculin powder (Sephadex G-25 Chromatography in Table 1).

The protein content, the activity yield and the purification degree obtained at each purification step are shown in Table 1.

TABLE 1

|  | Protein content (g) | Activity yield (%) | Purification degree (-fold) |
| --- | --- | --- | --- |
| Freeze-dried fruit powder | 1000 | 100 | 1 |
| 0.05N sulfate extract solution | 18 | 80 | 45 |
| Amberblite IRC-50 Chromatography | 3 | 55 | 185 |
| Sephadex G-25 Chromatography | 1 | 36 | 432 |

Figure 1:
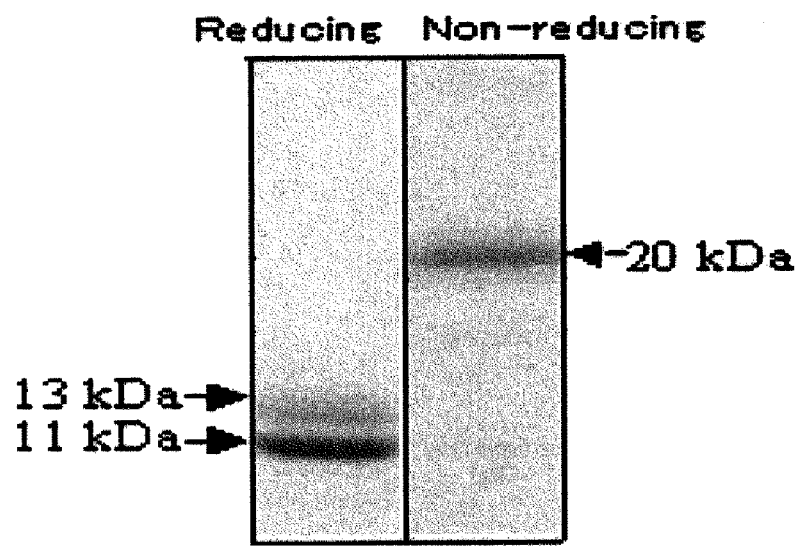
FIG. 1 shows a pattern obtained by subjecting purified neoculin powder to SDS-PAGE under reducing or non-reducing conditions and then staining the resulting products with CBB.

(4) Verification of Purification Results 2.5 μg of the purified neoculin powder obtained above in (1) to (3) was subjected to SDS-PAGE under reducing conditions or non-reducing conditions at a gel concentration of 15% and subsequently to CBB staining. As shown in FIG. 1, a single band was observed at a position of 20 kDa under non-reducing conditions, while under reducing conditions, two bands were observed at positions of 13 kDa and 11 kDa. This indicates that the resulting neoculin was highly purified and that neoculin was a dimer comprising the each subunit with 13 kDa and 11 kDa. Thus, the individual subunits were designated as neoculin acidic subunit (NAS) and neoculin basic subunit (NBS).

(5) Verification of Taste-modifying Activity 1.1 mg of the purified neoculin powder obtained above in (1) to (3) was subjected to Native-PAGE, using 10% acrylamide gel containing 6M urea. The resulting band was excised out. A sample extracted from the gel with water was freeze-dried. The freeze-dried sample was suspended in 150 μl of water. 50 μl of the resulting suspension was placed into the oral cavities of two panelists. The panelists verified that the sample had a sweet taste and that the sour taste of 0.02M citric acid after the panelists placed in the mouths and spewed out the sample was modified into sweet taste. Thus, it was confirmed that the sample had a taste-modifying activity.

Further, a 1/1000 volume of the recovered sample was subjected to SDS-PAGE, for staining with silver. A single band was observed at a position of 20 kDa, establishing the confirmation that the substance with the taste-modifying activity per se was neoculin.

EXAMPLE 2

Neoculin obtained in Example 1 was purified further by the following procedures, to make the analysis of the individual subunits constituting neoculin.

(1) Purification on HiTrap SP Sepharose Fast Flow Column 100 mg of the neoculin powder obtained in Example 1 was dissolved in 20 ml of buffer A (50 mM Tris-HCl buffer, pH 7.5 containing 8M urea and 30 mM DTT). Then, the whole volume was applied to HiTrap SP Sepharose Fast Flow column (manufactured by Amersham Biosciences; a 1.6 cm diameter×2.5 cm) equilibrated with the buffer A. Continuously, the column was washed with 50 ml of the buffer A. Continuously, elution was done with 50 ml of the buffer A containing 1M NaCl, to obtain a purified NBS fraction. Furthermore, 70 ml of the wash fraction was dialyzed against ion exchange water to a volume of 100 ml.

(2) Second Purification on HiTrap SP Sepharose Fast Flow Column

To 10.0 mg of the wash fraction obtained above in (1) was added 8 M urea, 30 mM DTT and 50 mM acetate buffer, pH 4.5 so as to be a total volume of 150 ml (all were expressed as final concentrations). The resulting mixture solution was applied to HiTrap SP Sepharose Fast Flow column (manufactured by Amersham Biosciences; a 1.6 cm diameter×2.5 cm) equilibrated with buffer B (50 mM acetate buffer, pH 4.5 containing 8 M urea and 30 mM DTT). Continuously, the column was washed with 50 ml of the buffer B, for elution with 50 ml of buffer B containing 1 M NaCl. Additionally, 200 ml of the wash fraction was dialyzed against ion exchange water to a volume of 250 ml.

(3) Purification on HiTrap DEAE Sepharose Fast Flow Column

To 250 mg of the wash fraction obtained above in (2) was added 8 M urea, 30 mM DTT and 50 mM Tris-HCl buffer, pH 9.0 so as to be a total volume of 350 ml (all were expressed as final concentrations). The resulting mixture solution was applied to HiTrap DEAE Sepharose Fast Flow column (manufactured by Amersham Biosciences; a 1.6 cm diameter×2.5 cm) equilibrated with buffer C (50 mM Tris-HCl buffer, pH 9.0 containing 8 M urea and 30 mM DTT). Continuously, the column was washed with 50 ml of the buffer C, for elution with 50 ml of buffer C containing 1 M NaCl, to obtain a purified NAS fraction.

(4) Verification of Purification Results

Figure 2:
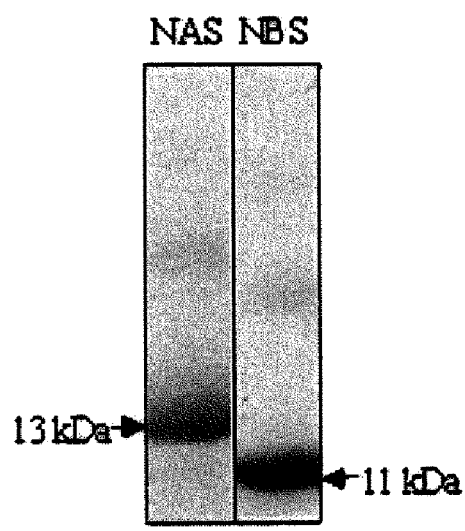
FIG. 2 shows a pattern obtained by subjecting purified powders of NAS and NBS to SDS-PAGE and then staining the resulting products with CBB.

The NBS fraction and the NAS fraction obtained above in (1) and (3) were individually dialyzed and freeze-dried, to obtain purified powders. 10 µg each of these purified powders was subjected to SDS-PAGE. As shown in FIG. 2, a single band was observed in the NAS fraction and the NBS fraction at positions of 13 kDa and 11 kDa, respectively. Thus, it was confirmed that each of the subunits was purified.

EXAMPLE 3

The amino acid sequence of the NAS fraction constituting neoculin as obtained in Example 2 was analyzed by the following procedures.

(1) Analysis of N-terminal Amino Acid Sequence

70 µg of the purified NAS powder obtained in Example 2(1) to (3) was subjected to two-dimensional electrophoresis. The gel after electrophoresis was overlaid on a polyvinylidene difluoride (PVDF) membrane, where an electric current passed vertically for transfer. The PVDF membrane after the transfer was stained with SYPRO Ruby protein blot stain (manufactured by Molecular Probes), from which bands were excised out by a general method for the analysis of the N-terminal amino acid sequence with an amino acid sequencer (HP G1005A Protein Sequencing System). In other words, phenylisothiocyanate (PITC) is allowed to react with a free amino residue at the N terminus to prepare a phenylthiocarbamyl derivative (PTC amino acid), which is then released with trifluoroacetic acid in the form of anilinothiazolinone-amino acid. Then, the anilinothiazolinone-amino acid is converted to a stable phenylthiohydantoin (PTH amino acid) in an acidic condition, for the analysis. In such manner, an amino acid sequence of 40 residues from the N terminus was determined.

(2) Analysis of Inner Amino Acid Sequence (i) S-Carboxyamide Methylation 10 mg of the purified NAS powder obtained in Example 2(1) to (3) was dissolved in 100 ml of 500 mM Tris-HCl buffer, pH 8.0 containing 6 M urea and 20 mM DTT. The resulting solution was left to standalone at 50° C. for one hour. 100 mg of iodoacetoamide was added to and mixed into the solution, which was then shaken in darkness at room temperature for 45 minutes. After the reaction solution was dialyzed and freeze-dried, NAS converted to S-carboxyamide methyl was obtained.

(ii) Fragmentation with Chymotrypsin

S-carboxyamide methylated NAS obtained above in (i) was digested with chymotrypsin in 0.1 M Tris-HCl buffer, pH 8.0 at 37° C. for 1.6 hours. The protein concentration was adjusted to 0.2 mg/ml while the ratio of the enzyme: the substrate was 1:20. The reaction was terminated by a processing at 100° C. for 3 minutes.

(iii) Fragmentation with Endoproteinase Asp-N

S-carboxyamide methylated NAS obtained above in (i) was digested with endoproteinase Asp-N in 50 mM phosphate buffer, pH 8.0 containing 0.01% SDS at 37° C. for 16 hours. The protein concentration was adjusted to 1.0 mg/ml while the ratio of the enzyme: the substrate was 1:100. The reaction was terminated by a processing at 100° C. for 3 minutes.

(iv) Fragmentation with Trypsin

S-carboxyamide methylated NAS obtained above in (i) was digested with trypsin in 0.1 M carbonate ammonium buffer, pH 8.5 containing 2 M urea at 37° C. for 24 hours. The protein concentration was adjusted to 0.2 mg/ml while the ratio of the enzyme: the substrate was 1:20. The reaction was terminated by a processing at 100° C. for 3 minutes.

(v) Peptide Separation and Sequence Analysis

The chymotrypsin-digested peptide, the endoproteinase Asp-N-digested peptide and the trypsin-digested peptide as obtained by the procedures above in (ii) to (iv) were separated by HPLC using TSKgel ODS-80TsQA column (manufactured by TOSOH; a 4.6 mm diameter×15 cm). The individual peptides were eluted by an elution method on a linear gradient of acetonitrile containing 0.05% trifluoroacetic acid.

Figure 3:
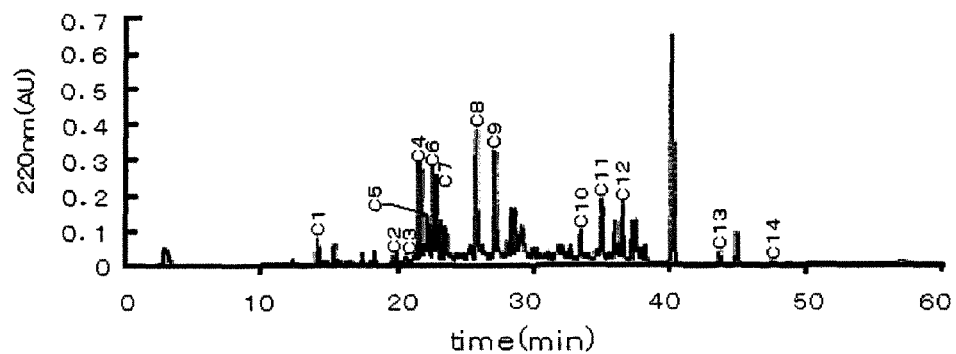
FIG. 3 is an HPLC separation of peptides obtained with chymotrypsin-digestion from S-carboxyamide methylated NAS.
Figure 4:
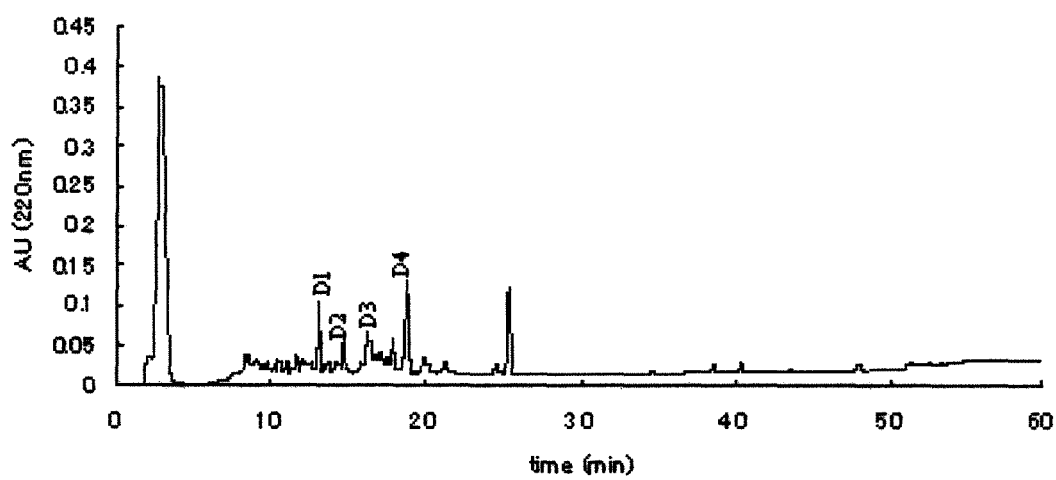
FIG. 4 is an HPLC separation of peptides obtained with endoproteinase Asp-N from S-carboxyamide methylated NAS.
Figure 5:
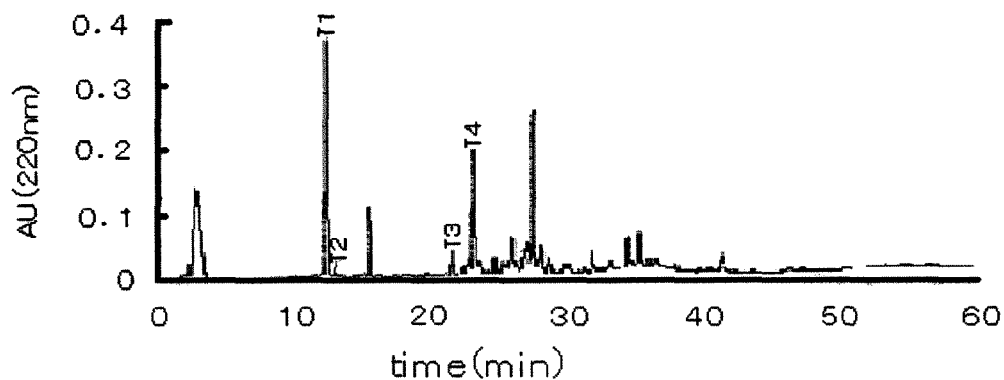
FIG. 5 shows a chart of the quantitative analysis of free amino acids via trypsin digestion of S-carboxyamide methylated NAS.

FIG. 3 shows the HPLC elution pattern of the chymotrypsin-digested peptide as detected at absorbance at 220 nm; FIG. 4 shows the HPLC elution pattern of the endoproteinase Asp-N-digested peptide as detected in the same manner as described above; and FIG. 5 shows the HPLC elution pattern of the trypsin-digested peptide as detected in the same manner as described above.

The peptides detected at 220 nm absorbance and isolated were dried and subsequently analyzed of the inner amino acid sequences with an amino acid sequencer (Procise 491cLC Protein Sequencing System or Procise 492HT Protein Sequencing System).

(3) Analysis of C-terminal Amino Acid Sequence 1 nmol of the S-carboxyamide methylated NAS obtained above in (2) (i) was digested with carboxypeptidase A in 50 mM Tris-HCl buffer, pH 7.5 containing 0.15% SDS at 25° C. The protein concentration was adjusted to 5 mg/ml, while the ratio of the enzyme: the substrate was 1:40. Immediately after the start of the reaction and 6 hours after the reaction, sampling was done. An equal volume of 10% trichloroacetic acid was added to the reaction solution to terminate the reaction. The reaction solution was left to stand alone at 0° C. for 30 minutes and then centrifuged, to recover the supernatant.

Amino acids released in the supernatant were modified into PTC amino acids, for quantitative analysis by HPLC using TSKgel ODS-80 TsQA column (manufactured by TOSOH; a 4.6 mm diameter ×15 cm). The results are shown in FIG. 6.

Figure 6:
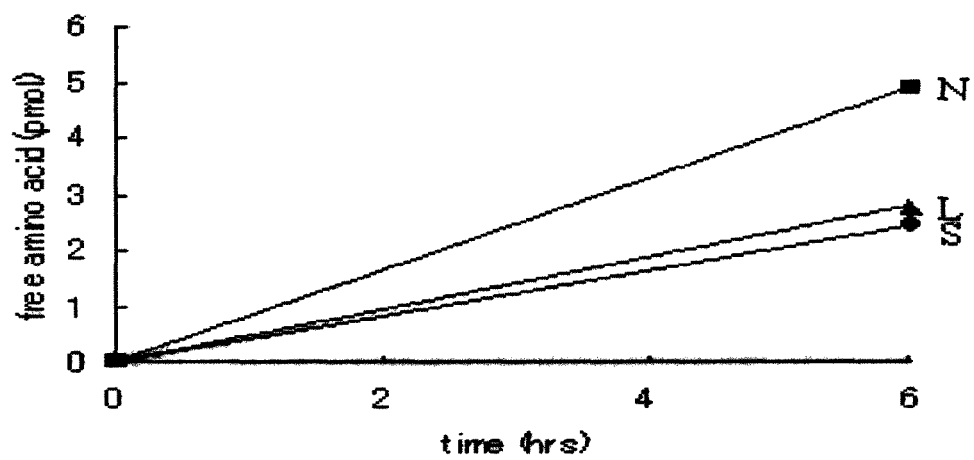
FIG. 6 shows the quantitative analysis of free amino acids from S-carboxyamide methylated NAS (1 nmol) via digestion with carboxypeptidase A.

As shown in the results in FIG. 6, amino acids except Asn, Leu and Ser were never released. Because carboxypeptidase A has a far lower activity to release Pro or Arg, the fourth amino acid residue from the C terminus might speculatively be Pro or Arg. Thus, it was confirmed that the C-terminal sequence of NAS was NLSP/R from the C terminus.

(4) Determination of Primary Structure

The amino acid sequence determined by the methods is as shown in SEQ ID NO.2 in the sequence listing and in FIG. 7. In FIG. 7, herein, N in the line 4 represents an amino acid sequence portion determined from the N terminus, while C1-14 represent amino acid sequences of peptides obtained by the chymotrypsin digestion; D1-4 represent amino acid sequences of peptides obtained by the endoproteinase Asp-N digestion; and T1-4 represent amino acid sequences of peptides obtained by the trypsin digestion. Additionally, the arrow ← represents an amino acid sequence resulting from the C terminus.

EXAMPLE 4

The amino acid sequence of the NBS fraction constituting neoculin as obtained in Example 2 was analyzed by the same procedures as in Example 3.

Consequently, the amino acid sequence of NBS was shown in SEQ ID NO.6 in the sequence listing and therefore, the amino acid sequence almost completely corresponds to the amino acid sequence of curculin B as a polypeptide already disclosed in JP-A-Hei 6-189771. However, the number of the amino acid residues of the NBS was larger by one residue than the number of the amino acid residues of curculin B, which was 114, because the amino acid sequence of the NBS includes one extra Gly added to the C terminus.

EXAMPLE 5

The sugar chain of the NAS fraction constituting neoculin as obtained in Example 2 was analyzed by the following procedures.

In other words, the peptide with the sugar chain-glycosylated consensus sequence, namely the chymotrypsin-digested peptide C1 of the purified NAS as obtained in Example 3(2)(ii) was recovered, to analyze the sugar composition of the sugar chain using an ABEE sugar composition analysis kit plus S (manufactured by Honen Corporation).

Specifically, the peptide was treated for the release of sialic acid; then, the sugar was converted to a reduced sugar, which was continuously hydrolyzed with an acid, to cleave all the glycoside bonds contained in the sugar chain of the glycoprotein, whereby releasing the sugars in the forms of monosaccharides. After the generated monosaccharides were labeled and then separated by HPLC using TSKgel ODS-80TsQA column (manufactured by TOSOH; a 4.6 mm diameter×7.5 cm), detection was performed by 305 nm absorbance for analysis.

As the results of the analysis, the sugar composition of the sugar chain added to NAS was mannose/N-acetylglucosamine/fucose/xylose at a ratio of about 3/2/1/1. FIG. 8 shows the results and a sugar chain structure glycosylated NAS as speculated with reference to sugar chain structures observed generally in plants.

EXAMPLE 6

The gene encoding NAS constituting neoculin was cloned by the following procedures.

(1) Preparation of cDNA Library

As a material, a fruit of *Curculigo latifolia* (supplied from the Yamashina Plant Data Institute, Nippon Shinyaku) was used. About 20.6 g of the fruit aged 4 weeks to 8 weeks after pollination was frozen in liquid nitrogen, which was then ground while avoiding thawing. Using 20.6 g of the powder obtained in such manner as a sample, Poly(A) +mRNA was extracted by mRNA Purification Kit (manufactured by Amersham Bioscience).

From about 4.5 μg of the extracted mRNA, a cDNA library was prepared using cDNA Synthesis Kit (manufactured by Amersham Bioscience). cDNA was inserted via EcoRI adaptor conjugation into λZAPII vector (manufactured by Stratagene). The vector was packaged in a phage using Gigapack III Gold Packaging Extract (manufactured by Stratagene), which was allowed to infect *Escherichia coli* XL1-Blue MRF'. Thus, a library of about $1.2 \times 10^5$ plaques was prepared.

(2) Preparation of Probe

Using 20 mg of the freeze-dried fruit of *Curculigo latifolia* as a material, the genome DNA was extracted, using DNeasy Plant Mini Kit (manufactured by QIAGEN). Based on the amino acid sequence of NBS as disclosed in JP-A-Hei 6-189771, the NC1S primer shown in SEQ ID NO.4 in the sequence listing, and the NC1A primer shown in SEQ ID NO.5 in the sequence listing were synthetically prepared. Using the extracted genome DNA as template, PCR was done (one cycle of 94° C. for 3 minutes, 42° C. for 3 minutes, and 72° C. for 3 minutes and 50 cycles of 94° C. for 30 seconds, 42° C. for 30 seconds and 72° C. for one minute). A 469 bp DNA fragment encoding a part of NAS was obtained. The DNA fragment was used as probe.

(3) Plaque Hybridization $2 \times 10^4$ plaques in the library obtained in (1) were transferred onto a nylon membrane to immobilize DNA. Using subsequently the probe prepared in (2), hybridization was done at 65° C. Using 0.1×SSC and 0.1% SDS, rinsing was done at 65° C. Consequently, about 100 plaques were hybridized with the probe. 25 plaques with more intense signals were subjected to secondary screening, for separation into single plaque.

(4) Determination of Nucleotide Sequence

The single plaque phage obtained in (3) was co-infected with a helper phage and XL1-Blue MRF', for in vivo excision. Then, a pBluescriptII SK(−) containing the insert cDNA was excised out from the λZAPII vector. The nucleotide sequence of cDNA was determined by dideoxy method.

Consequently, the nucleotide sequence thus determined was as shown in SEQ ID NO.1 in the sequence listing. The amino acid sequence of a polypeptide encoded by a nucleotide sequence comprising the nucleotides 70 to 408 in the nucleotide sequence shown in SEQ ID NO.1 in the sequence listing coincided with the amino acid sequence (the amino acid sequence shown in SEQ ID NO.3 in the sequence listing) of the NAS as obtained in Example 4.

Additionally, an open reading frame (ORF) including the amino acid sequence of NAS was found in a part of the nucleotide sequence shown in SEQ ID NO.1 in the sequence listing, which part comprises the nucleotides 4 to 477. It was verified that NAS was generated as a precursor peptide (PNAS) containing a signal peptide and an extension peptide. The amino acid sequence of PNAS encoded by the nucleotide sequence comprising the nucleotides 4 to 477 therein is shown in SEQ ID NO.3 in the sequence listing.

EXAMPLE 7

A vegetable juice was prepared by the following procedures, where neoculin was to be added. The taste-modifying activity was evaluated.

300 ml of water was added to finely cut fresh spinach, green pepper, celery of 135 g, 65 g and 65 g, respectively and 25 g of lemon juice. The resulting mixture was processed in a blender for 5 minutes and then filtered through a nylon mesh with pore size of 0.1 mm, to obtain about 400 ml of a vegetable juice. To 100 ml of the resulting vegetable juice was added 50 mg of the purified neoculin powder obtained in Example 1. The resulting juice was designated as high concentration-added vegetable juice. 10 mg of the purified neoclin powder was added to 100 ml of the vegetable juice, which was designated as low concentration-added vegetable juice. The vegetable juice without any addition was designated as control sample. Four panelists made an organoleptic evaluation. While the bitterness, astringency and sweetness of the vegetable juice without any addition were ranked as score 0 as evaluation score, great enhancement of the individual tastes was marked with score 2; simple enhancement thereof was marked with score 1; great reduction thereof was marked with score −2; and simple reduction thereof was marked with score −1. The mean of the evaluation results is shown in Table 2.

TABLE 2

|  | Bitterness | Astringency | Sweetness |
| --- | --- | --- | --- |
| Vegetable juice without any addition | 0 | 0 | 0 |
| High concentration-added vegetable juice | −1.75 | −1.25 | 1.5 |
| Low concentration-added vegetable juice | −1.0 | −0.75 | 1.0 |

From the results in Table 2, it was verified that the neoculin of the invention reduced bitterness and astringency greatly and gave sweetness, so that the neoculin had an effect of enhancing the taste of foods.

EXAMPLE 8

A grapefruit juice was prepared by the following procedures, where neoculin was to be added. The taste-modifying activity was evaluated.

To 100 ml of a grapefruit juice was added 10 mg of the purified neoculin powder obtained in Example 1, which was defined as a high concentration-added sample. A sample prepared by adding 5 mg of the neoculin powder was defined as a low concentration-added sample, while the grapefruit juice without any addition was defined as control sample. Four panelists made an organoleptic evaluation. While the bitterness, astringency and sweetness of the vegetable juice without any addition were ranked as score 0 as evaluation score, great enhancement of the individual tastes was marked with score 2; simple enhancement thereof was marked with score 1; great reduction thereof was marked with score −2; and simple reduction thereof was marked with score −1. The mean of the evaluation results is shown in Table 3.

TABLE 3

|  | Bitterness | Astringency | Sweetness |
| --- | --- | --- | --- |
| Sample without any addition | 0 | 0 | 0 |
| High concentration-added sample | −1.75 | −1.25 | 1.5 |
| Low concentration-added sample | −1.0 | −0.5 | 0.75 |

From the results in Table 3, it was verified that the neoculin of the invention greatly reduced bitterness and suppresses sourness and gave sweetness, so that the neoculin had an effect of enhancing the taste of foods.

EXAMPLE 9

A seasoning liquid for sushi neta (sushi topping) was prepared by the following procedures, where neoculin was to be added. The taste-modifying activity thereof was evaluated. The seasoning liquid for sushi neta as referred to herein is a seasoning for seasoning sushi neta, by preliminarily coating raw sushi neta or once heat-treated sushi neta or immersing sushi neta therein.

The composition of the seasoning liquid for sushi neta was as shown in Table 4. Further, the seasoning liquid for sushi neta was diluted two-fold for use in this Example, because seasoning liquids for sushi neta are appropriately diluted with water, depending on the kind and amount of sushi neta in use.

TABLE 4

| Raw materials | Blended amount (% by weight) |
| --- | --- |
| Brewed vinegar | 18 |
| Hydrogenated saccharified-starch syrup | 13 |
| pH adjuster | 8 |
| Seasoning (amino acid) | 4 |
| Edible salt | 4 |
| water | 53 |

To 100 ml of the diluted seasoning liquid for sushi neta was added 11.3 mg of the purified neoculin powder obtained in Example 1, to obtain a neoculin-added seasoning liquid. Shrimp was immersed in the neoculin-added seasoning liquid for 20 minutes, to obtain sushi neta of shrimp (neoculin-added sample). Alternatively, shrimp was immersed in the diluted seasoning for sushi neta in the same manner but without any addition of the neoculin powder to obtain sushi neta of shrimp (control sample). Four panelists ate each one of the neoculin-added sample and the control sample, to evaluate the intensity of the astringency of each of the samples. Consequently, it was confirmed that astringency was highly suppressed in the neoculin-added sample, compared with the control sample.

EXAMPLE 10

The taste-modifying activity of neoculin and the taste-modifying activity of curculin were compared together by the following procedures.

(1) Preparation of Curculin

Curculin B was expressed by the method disclosed in Examples 1 through 12 in JP-A-Hei 6-189771.

Subsequently, a transformant *Escherichia coli* expressing curculin B was disrupted with an ultrasonic generator to prepare a suspension, which was centrifuged four times using 25 mM phosphate buffer, pH 6.8 containing 50 mM sodium chloride, for washing. The resulting suspension was dissolved in 500 mM Tris-HCl, pH 9.5 containing 8 M urea and 10 mM DTT, for 2.5-hour reduction at 37° C. To the solution was added a 10-fold volume of 500 mM Tris-HCl, pH 8.5 containing 8 M urea and 0.11 M glutathione in the oxidized form. The resulting mixture was left to stand at room temperature for 3 hours, to glutathionylate the protein. To the glutathionylated protein was added a 10-fold volume of 50 mM Tris-HCl buffer, pH 9.0 containing 4 mM cysteine, for reaction at 4° C. for 2 days and subsequent dialysis against 50 mM phosphate buffer, pH 6.8 containing 0.1 M sodium chloride, to form a homodimer. Subsequently, the homodimer was freeze-dried, to obtain a curculin powder as a homodimer of curculin B.

Figure 9:
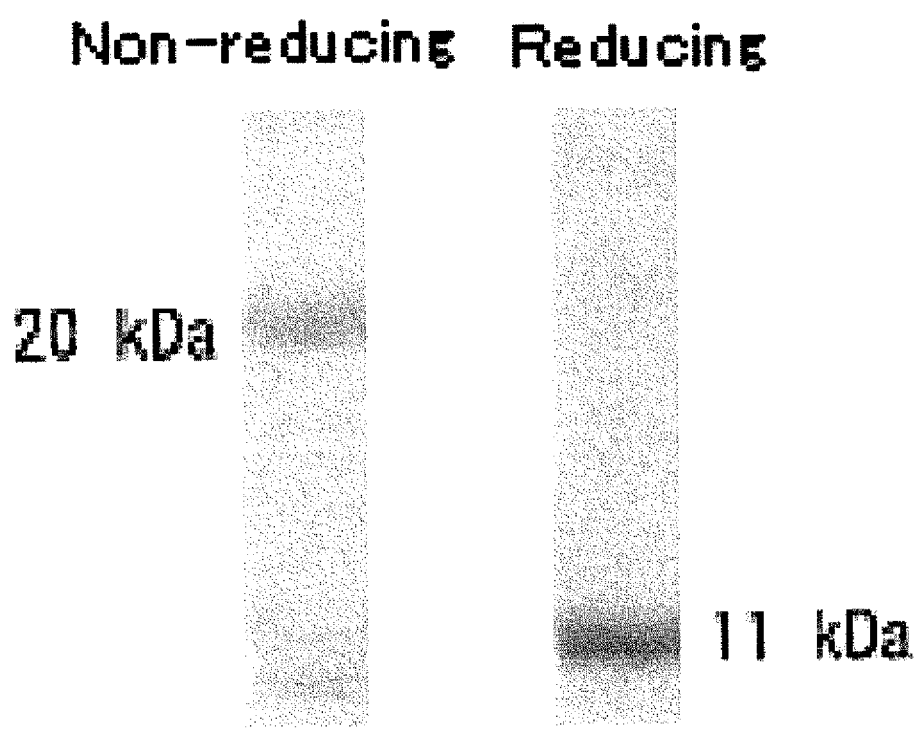
FIG. 9 shows a pattern obtained by subjecting curculin to SDS-PAGE under reducing or non-reducing conditions and then staining the resulting products with CBB.

It was verified by SDS-PAGE that curculin B formed a homodimer. Specifically, 10 μg of the curculin powder was subjected to SDS-PAGE at a gel concentration of 15% and subsequently to CBB staining, so that as shown in FIG. 9, a single band was observed under non-reducing conditions at a position of about 20 kDa, while it was confirmed that one band was observed at a position of about 11 kDa under reducing conditions. Using the homodimer curculin, the following organoleptic test was done.

(2) Comparison of Taste-modifying Activity

The purified neoculin obtained in Example 1 was dissolved in water to the individual concentrations of 30, 50, 75 and 100 μg/ml, while curculin obtained in (1) was dissolved in water to 100 μg/ml. Using the sweetness felt when 0.1 v/v % acetic acid was then placed in the mouth after 500 μl of the 100 μg/ml curculin solution was once placed in the mouth and then discharged therefrom as a basis, the sweetness felt when 0.1 v/v % acetic acid was then placed in the mouth after 500 μl of a neoculin solution at each of the concentrations was once placed in the mouth and then discharged therefrom was evaluated by 3 panelists. Compared with the sweetness using the curculin solution, the sweetness at the same level was marked with score 0; slightly stronger sweetness was marked with score 1; stronger sweetness was marked with score 2; far stronger sweetness was marked with score 3; slightly weaker sweetness was defined as −1; weaker sweetness was marked with score −2; far weaker sweetness was defined as −3. The mean of the evaluation results is shown in Table 5.

TABLE 5

| | Neoculin concentration (μg/ml) | | | |
|---|---|---|---|---|
| | 30 | 50 | 75 | 100 |
| Evaluation score | 1.33 | 2.33 | 2.5 | 3.0 |

The results in Table 5 show that the taste-modifying activity of neoculin was far stronger than the taste-modifying activity of curculin.

EXAMPLE 11

Using a vector carrying the DNA of the gene encoding NAS and a vector carrying the DNA of the gene encoding NBS, neoculin expression in a koji mold was verified.

For the generation of a heterologous protein using a filamentous fungus such as *Aspergillus oryzae* as one of koji mold, the foreign protein is expressed as a fusion protein with a protein secreted from a host, so that the generation can be done at a large scale. By inserting a sequence cleaved from KEX2 as a protease localizing in the Golgi body, only the intended protein can be secreted (see for example, Appl. Environ. Microbiol., Vol. 63, p. 488-497, 1997).

In this Example, neoculin was produced by expressing the gene encoding NAS and the gene encoding NBS, using α-amylase as a protein secreted at the large quantity in *Aspergillus oryzae* as a carrier.

The expression was done by the procedures described below.

(1) Preparation of Recombinant Vector

Using a vector construction kit (Multisite Gateway Three-Fragment Vector Construction Kit; manufactured by Invitrogen), recombinant vectors (pgFa3GNaSJ and pgFa3GNbTa) were prepared.

The method using the kit was progressed for construction of recombinant vectors in an order of (a) the preparation of 5' entry clone, (b) the preparation of the entry clone of an intended gene, (c) the preparation of 3' entry clone, and (d) the preparation of an expression vector via the recombination between the three types of entry clones and a destination vector.

Specifically, the method was carried by the following procedures under the following conditions.

(a) Preparation of 5' Entry Clone

According to the method of Mahashi, et al. (see for example, the proceedings of the annual meeting 2004 of Japan Agricultural and Biological Chemistry Association, p. 24, 2004), the 5' entry clone (pg5'PFa) was prepared.

Specifically, using the genome of an *Aspergillus oryzae* strain RIB40 (available under storage as RIB No.40 at the National Research Institute of Brewing) as template, with a use of primer 1 comprising the nucleotide sequence shown in SEQ ID NO.7 in the sequence listing (5'-GGGGACAACTTTGTATAGAAAAGTTGATGCATT TCATGGTGTTTTGATCATT-3'; the sequence of the attB site is underlined) and primer 2 comprising the nucleotide sequence shown in SEQ ID NO.8 in the sequence listing (5'-GGGGACTGCTTTTTTGTACAAACTTGTCGAGCTAC-TACAGATCTTGCTA-3'; the sequence of the attB site is underlined), PCR was done to amplify the amyB promoter and the sequence of the ORF.

An amplified fragment obtained by PCR was introduced into a donor vector pDONR P4-P1R (manufactured by Invitrogen) utilizing the recombination between the attB site and the attP site (BP recombination), and a 5' entry clone (referred to as pg5'PFa hereinafter) was obtained. Subsequently, pg5'PFa was introduced in *Escherichia coli* strain DH5α, and a plasmid was extracted from the resulting colony.

(b) Preparation of the Entry Clone of an Intended Gene

The entry clone (pgE3GNa) of the, gene encoding NAS among the intended genes was prepared as follows. Using the mature region of NAS (a part encoding $^{23}$Asp to $^{135}$Asn; a part comprising the nucleotides 70 to 408 in the nucleotide sequence shown in SEQ ID NO.1 in the sequence listing) as template among the cDNA clones of the gene encoding NAS, PCR was done using primer 3 comprising the nucleotide sequence shown in SEQ ID NO.9 in the sequence listing as designed by adding the KEX2-cleavage sequence (Lys-Arg) and three Gly residues before the N terminus (5'-GGGGACAAGTTTGTACAAAAAAGCAGGCTCTAAA-CGTGGGGGGGGGGACAGTGTCCTGCTCT CC-3'; the sequence of the attB site is underlined) and primer 4 comprising the nucleotide sequence shown in SEQ ID NO.10 in the sequence listing as designed by adding a nucleotide sequence including a termination codon after the C terminus (5'-GGGGACCACTTTGTACAAGAAAGCTGGGTTTAATT-AAGACTGCGGCACCC-3'; the sequence of the attB site is underlined).

An amplified fragment obtained by PCR was introduced through BP recombination into a donor vector pDONR221 (manufactured by Invitrogen), to obtain the entry clone of the gene encoding NAS (referred to as pgE3GNa hereinafter). Subsequently, pgE3GNa was introduced in *Escherichia coli* strain DH5α, and a plasmid was extracted from the resulting colony.

The entry clone (pgE3GNb) of the gene encoding NAS was prepared essentially in the same manner as in the case of the gene encoding NAS. Specifically, using the mature region of NBS (a part encoding $^{23}$Asp to $^{137}$GLy; a part comprising the nucleotides 67 to 411 in the nucleotide sequence shown in SEQ ID NO.17 in the sequence listing) as template among, the cDNA clones of the gene encoding NBS, PCR was done using primer 5 comprising the nucleotide sequence shown in SEQ ID NO.11 in the sequence listing as designed by adding the KEX2-cleavage sequence and three Gly residues before the N terminus (5'-GGGGACAAGTTTGTACAAAAAAGCAGGCTCTAAA CGTGGGGGGGGGGACAGTGTCCTGCTCTCCG-3'; the sequence of the attB site is underlined) and primer 6 comprising the nucleotide sequence shown in SEQ ID NO.12 in the sequence listing as designed by adding a nucleotide sequence including a termination codon after the C terminus (5'-GGGGACCACTTTGTACAAGAAAGCTGGGTT TATC-CACCATTAACACGGCG-3'; the sequence of the attB site is underlined.).

An amplified fragment obtained by PCR was introduced through BP recombination into a donor vector pDONR221 (manufactured by Invitrogen), to obtain the entry clone of the gene encoding NBS (referred to as pgE3GNb hereinafter). Subsequently, pgE3GNb was introduced in *Escherichia coli* strain DH5α, and a plasmid was extracted from the resulting colony.

(c) Preparation of 3' Entry Clone

According to the method of Mahashi, et al. (see for example the proceedings of the annual meeting 2004 of Japan Agricultural and Biological Chemistry Association, p. 24, 2004), the 3' entry clones (pg3'sCJ and pg3'Ta) were prepared.

First, the 3' entry clone with integrated amyB terminator and the sC gene of *Aspergillus nidulans* was obtained in the following manner. Using pgDSN (a plasmid with the amyB terminator and the sequence of the ATP sulfurylase (sC) gene of *Aspergillus nidulans* (the nucleotide sequence shown in SEQ ID NO.18 in the sequence listing) as integrated therein) as template, specifically, PCR was done using primer 7 shown in SEQ ID NO.13 in the sequence listing (5'-GGGGACAGCTTTCTTGTACAAAGTGGGTGATCTGT-AGTAGCTCGTGAA-3'; the sequence of the attB site is underlined) and primer 8 shown in SEQ ID NO.14 in the sequence listing (5'-GGGGACAACTTTGTATAATAAAGTTG-GATC-TTGGATATAA AAATCCAAATATG-3'; the sequence of the attB site is underlined), to amplify the amyB terminator and the sequence of the sC gene of *Aspergillus nidulans*.

An amplified fragment obtained by PCR was introduced into a donor vector pDONRP2R-P3 (manufactured by Invitrogen) utilizing BP recombination, to obtain a 3' entry clone (referred to as pg3'sCJ hereinafter). Subsequently, pg3'sCJ was introduced in *Escherichia coli* strain DH5α, and a plasmid was extracted from the resulting colony.

Additionally, a 3' entry clone (pg3'Ta) with the amyB terminator alone was prepared by the same procedures as above for pg3'sCJ.

Using the nucleotide sequence shown in SEQ ID NO.18 in the sequence listing as template, PCR was done using primer 9 comprising the nucleotide sequence shown in SEQ ID NO.15 in the sequence listing as designed (5'-GGGGA-CAGCTTTCTTGTACAAAG TGGGATCTGTAG-TAGCTCGTGAAG-3'; the sequence of the attB site is underlined) and primer 10 comprising the nucleotide sequence shown in SEQ ID NO.10 in the sequence listing (5'-GGGGACAACTTTGTATAATAAAGTTGTTTCCTATAA-TAGACTAGCGTGC-3'; the sequence of the attB site is underlined.).

An amplified fragment obtained by PCR was introduced through BP recombination into a donor vector pDONRP2R-P3 (manufactured by Invitrogen), to obtain the 3'entry clone (referred to as pg3'Ta hereinafter). Subsequently, the entry clone was introduced into *Escherichia coli* strain DG5α, to obtain a colony, which was then amplified for plasmid extraction.

(d) Preparation of an Expression Vector Via the Recombination Between the Three Types of Entry Clones and a Destination Vector A recombinant vector with the DNA of the gene encoding NAS as introduced therein, namely NAS expression vector (referred to as pgFa3GNaSJ hereinafter) was prepared as follows.

The three types of entry clones, namely pg5'PFa obtained above in (a), pgE3GNa obtained above in (b) and pg3'sCJ obtained above in (c) were mixed with a destination vector pDESTR4-R3 (manufactured by Invitrogen), to which LR Clonase Plus Enzyme Mix was added to promote the recombination between the attL site and the attR site (LR recombination). The recombinant vector thus obtained was introduced into *Escherichia coli* strain DH5α for transformation. The resulting colony was amplified to extract the intended recombinant vector pgFa3GNaSJ.

Figure 10:
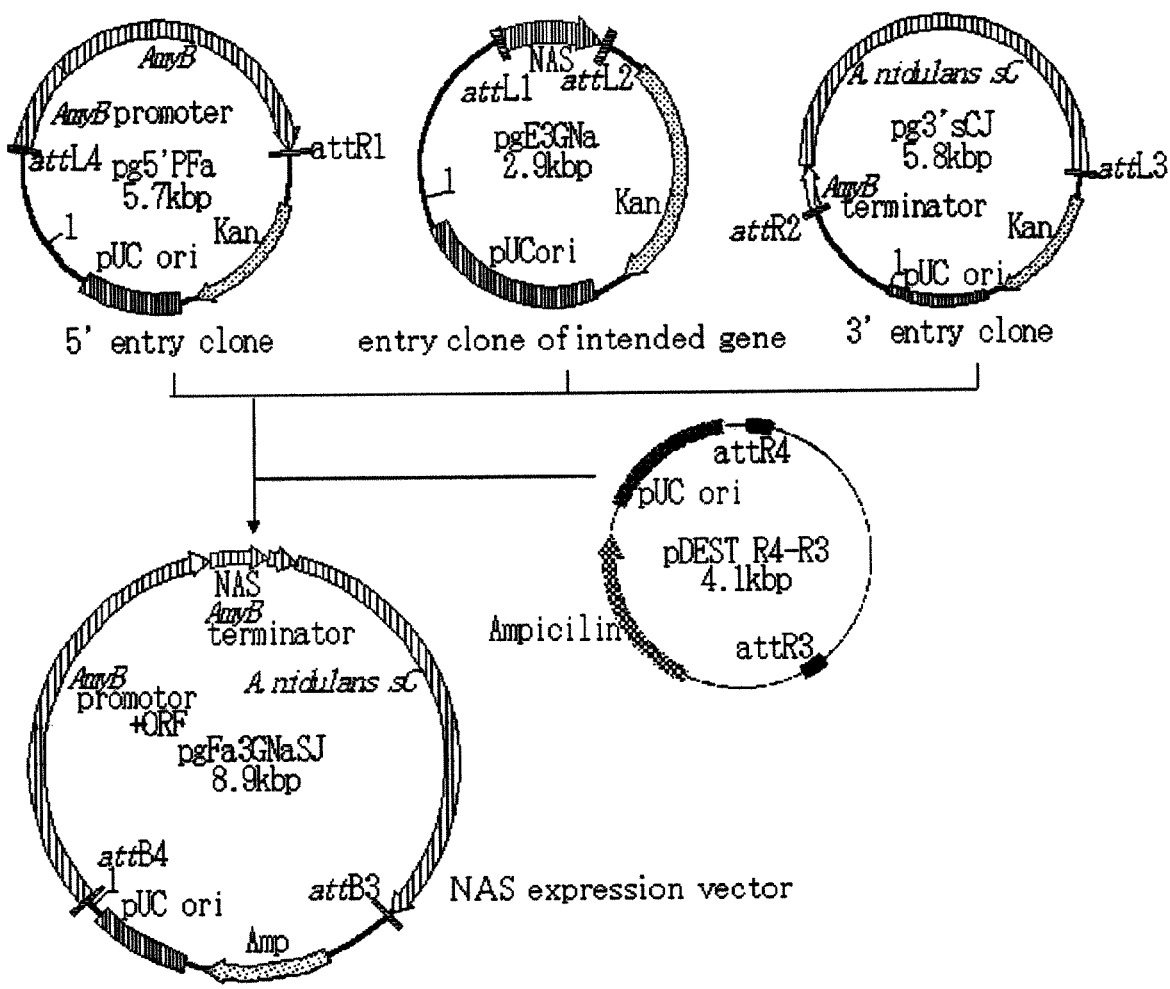
FIG. 10 depicts a schematic view of the method for preparing an expression vector for NAS.

The preparation process and structure of such pgFa3GNaSJ are shown in FIG. 10.

The recombinant vector with the DNA of the gene encoding NBS as introduced therein, namely NBS expression vector (referred to as pgFa3GNbTa hereinbelow) was prepared as follows.

The three types of entry clones, namely pg5'PFa obtained above in (a), pgE3GNb obtained above in (b) and pg3'Ta obtained above in (c) were mixed with a destination vector pDESTR4-R3 (manufactured by Invitrogen), to which LR Clonase Plus Enzyme Mix was added to promote LR recombination. The recombinant vector thus obtained was introduced into *Escherichia coli* strain DH5α for transformation. The resulting colony was amplified to extract the intended recombinant vector pgFa3GNbTa.

Figure 11:
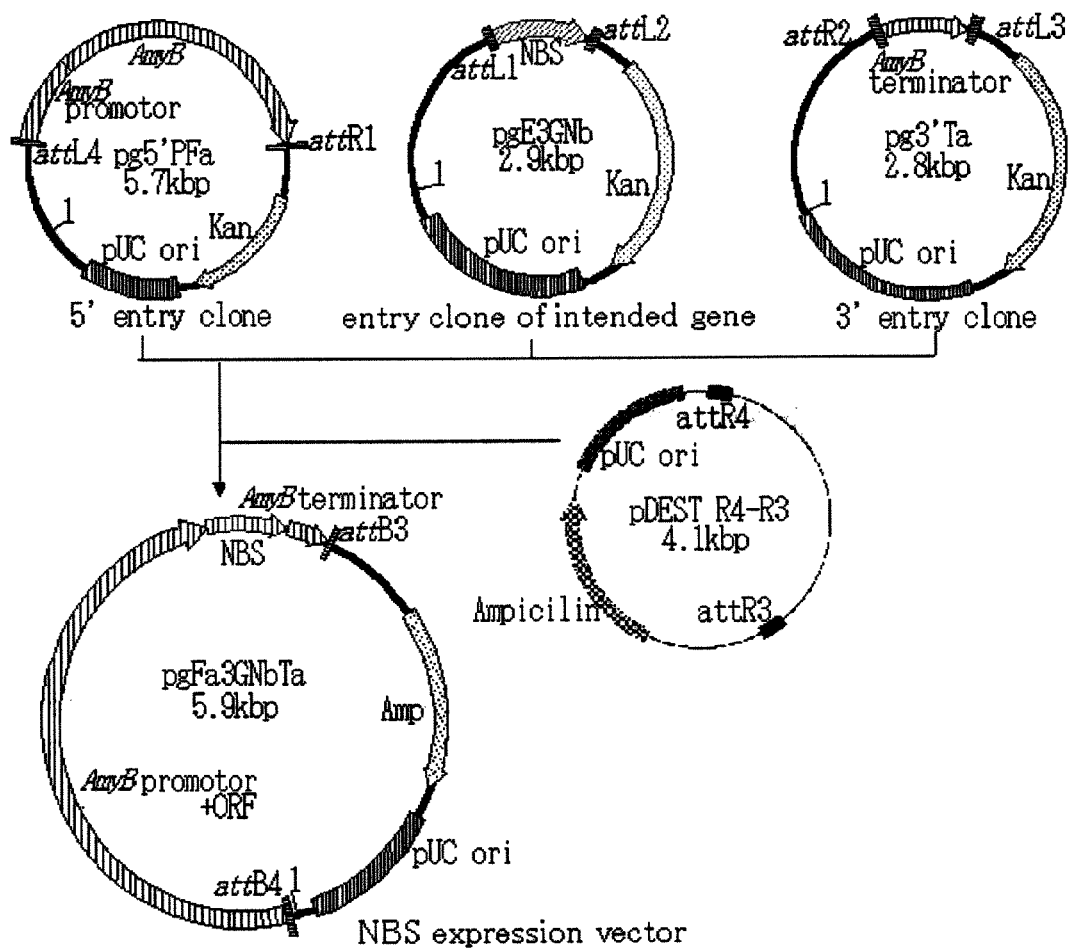
FIG. 11 depicts a schematic view of the method for preparing an expression vector for NBS.

The preparation process and structure of such pgFa3GNbTa are shown in FIG. 11.

The recombinant vectors thus obtained (pgFa3GNaSJ and pgFa3GNbTa) have the following three characteristic features. A first feature is the use of α-amylase as a carrier protein to express a fusion protein between NAS and NBS with α-amylase, by introducing the gene encoding α-amylase together with the genes encoding NAS and NBS.

In case that a protein is to be generated in a heterologous host except the original biological organism, particularly in case that *Aspergillus oryzae* is used as the host, a report tells about the use of glucoamylase (GlaA), which is a secretory protein of the host as a carrier, resulting in the increase in the productivity (Biosci. Biotechnol. Biochem., Vol. 58, No.5, p. 895-899, 1994). However, no examination has been made yet about the use of other secretion proteins as carriers. The inventors made an attempt to stabilize a foreign protein in the secretion process and increase the productivity, using α-amylase as the enzyme secreted in the large amount from *Aspergillus oryzae*.

A second feature is the introduction of a KEX2 recognition sequence (Lys-Arg) in a part where α-amylase is conjugated with NAS or NBS.

KEX2-like protease exists in the Golgi body of koji mold. KEX2 protease is a serine protease recognizing basic amino acid pairs (Lys-Lys, Lys-Arg, Arg-Lys, and Arg-Arg; the recognition sequences of KEX2) and cleaving the C terminus. In other words, when a protein with these recognition sequences of KEX2 is transferred from endoplasmic reticulum (ER) to the Golgi body, KEX2-like protease cleaves the protein in the Golgi body. Thus, the fusion protein is cleaved at the site of KEX2 recognition site introduced between α-amylase and NAS or NBS (processing), to obtain NAS or NBS singly.

A third feature is the improvement of the cleavage efficiency.

The cleavage with KEX2 may sometimes be done inaccurately because of steric structures around the recognition sequences of KEX2. Because it was speculated that neoculin forms a heterodimer and the steric structures around the cleavage site may be complicated, three Gly residues were inserted immediately before Asp at the N termini of NAS and NBS, to improve the cleavage efficiency and the cleavage accuracy.

(2) Preparation of Transformant

Transformation was done in the following manner by a modification of the method of Punt et al. (Methods Enzymol. Vol. 216, p. 447-457, 1992).

(a) Preparation of Protoplast

On a PD plate (39 g of potato dextrose (manufactured by Nissui) was dissolved in one liter of water and then autoclaved, and was then divided in a sterile plate), with a sterile skewer was spread on the plate *Aspergillus oryzae* strain NS4 (sC, niaD) for incubation at 30° C. for 7 days, to grow a conidiospore. This was scratched into 100 ml of DPY culture broth (2% dextrin, 1% polypeptone, 0.5% yeast extract, 0.5% $KH_2PO_4$, 0.05% $MgSO_4.7H_2O$, pH 5.5) using a bamboo skewer for shaking culturing at 30° C. and 200 rpm for 20 hours. Subsequently, the bacterial cells were recovered with a sterile Miracloth (manufactured by Calbiochem) and rinsed in sterile water.

The cells were transferred into an L-shape test tube placing therein 10 ml of Sol-1 (1% Yatalase (manufactured by Takara Brewery), 0.6 M $(NH_4)_2SO_4$, 50 mM maleate buffer, pH 5.5), for gentle shaking at 30° C. for 3 hours, to prepare a protoplast.

(b) Introduction of Expression Vector—Co-Transformation of an Appropriate Volume of Expression Vector, Screening on an Auxotrophic Culture Medium and Stabilization, of Character The resulting protoplast was passed through Miracloth to remove the cell debris, to which an equal volume of Sol-2 (1.2 M sorbitol, 50 mM $CaCl_2$, 35 mM NaCl, 10 mM Tris-HCl, pH 7.5 was added). The resulting mixture was centrifuged at 2000 rpm and 4° C. under break off.

After the precipitate was twice rinsed with Sol-2, the precipitate was suspended in 200 μl of Sol-2 to $1 \times 10^7$ cell/ml. Adding 2 μg of the NAS-introduced plasmid and 10 μg of the NBS-introduced plasmid, the resulting mixture was incubated on ice for 30 minutes. Adding 250 μl, 250 μl and 850 μl of Sol-3 (60% PEG4000, 50 mM $CaCl_2$, 10 mM Tris-HCl, pH 7.5) in a step-wise manner, the mixture was gently mixed together and then left to stand alone at ambient temperature for 20 minutes. Adding 5 to 10 ml of Sol-2, the mixture was centrifuged, for suspension in 500 μl of Sol-2.

The suspension was added to 5 ml of Top agar (supplemented with 1.2 M sorbitol) preliminarily divided and kept warm, and then poured onto the lower layer medium (MS plate; 1.2 M sorbitol, 0.2% $NH_4Cl$, 0.1% $(NH_4)_2SO_4$, 0.05% KCl, 0.05% NaCl, 0.1% $KH_2PO_4$, 0.05% $MgSO_4.7H_2O$, 0.002% $FeSO_4.7H_2O$, 2% glucose, 1.5% agar, pH 5.5).

Then, wrapping with a parafilm and opening an air hole, the culture medium was incubated at 30° C. for 3 to 5 days. The resulting colony was sub-cultured in the M plate (0.2% $NH_4Cl$, 0.1% $(NH_4)_2SO_4$, 0.05% KCl, 0.05% NaCl, 0.1% $KH_2PO_4$, 0.05% $MgSO_4.7H_2O$, 0.002% $FeSO_4.7H_2O$, 2% glucose, 1.5% agar, pH 5.5) three times, to stabilize the character. 30 transformant strains per one plate were obtained.

(3) Screening for Neoculin-generating Strain (a) Generation at Small Scale in DPY Culture Broth (pH 8.0) and Recovery of Liquid Culture 12 transformant strains obtained in the transformant preparation described above in (2) were spread on an M plate, for incubation at 30° C. for 2 to 4 days. Conidiospore was scratched and recovered with an autoclaved bamboo skewer, for culturing in a 100 ml flask charged with 20 ml of DPY culture broth, pH 8.0 (0.5% $KH_2PO_4$ was replaced with 0.5% $KH_2PO_4$ in the composition of the reagents in the DPY culture broth, pH 5.5, which was then adjusted to pH 8.0 using 1M NaOH) with shaking at 30° C. and 200 rpm for 3 days. The cells were separated and recovered from the liquid culture with a Miracloth.

(b) Screening for Generating Strain and Western Blotting Analysis

The recovered liquid culture was subjected to SDS-PAGE (15% acrylamide) under reducing conditions, transferred onto a PVDF film (manufactured by Millipore) and analyzed by western blotting.

The film after the transfer was soaked in TBST containing 5% skimmilk, for gentle shaking at room temperature for 60 minutes. 0.5 μl of an anti-neoculin antibody as a primary antibody was added to 2.5 ml of TBST containing 5% skim milk, and then placed in a plastic bag and left to stand alone therein at room temperature for 60 minutes. After the film was washed thrice with TBST for 10 minutes, 2.5 μl of alkali phosphatase-bound anti-rabbit IgG antibody (manufactured by Sigma) as a secondary antibody was added to TEST containing 5% skim milk and was then placed in a plastic bag, which was left to stand alone at room temperature for 60 minutes. After the film was washed thrice with TBST for 10 minutes, 66 μl of NBT and 33 μl of BCIP as substrates were added to 10 ml of a reaction solution (0.1 M Tris-HCl, pH 9.5, 5 mM $MgCl_2$, 0.1 M NaCl). The resulting mixture reacted together under a condition of light-shielding darkness for several minutes, for color reaction. The results are shown in FIG. 12.

Figure 12:
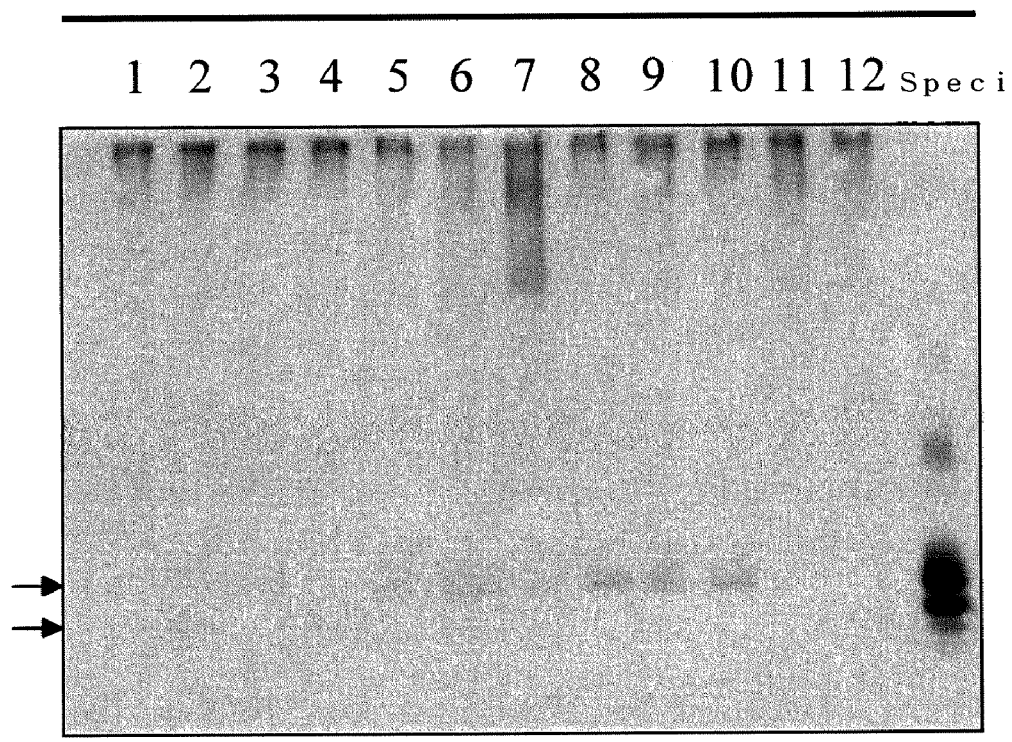
FIG. 12 shows a chart showing the results of the western blotting of a liquid culture of 12 transformant strains after SDS-PAGE under reducing conditions.

Consequently, the strain #2 was selected among the 12 transformant strains, taking account of the molecular weight of a neoculin specimen purified from *Curculigo* fruit and the ratio of the bands of the two subunits generated by the transformants (the arrow in FIG. 12). The strain #2 thus selected was designated as *Aspergillus oryzae* NS-NAB2 strain, and has been deposited as an accession No. FERM BP-10209 at the International Patent Organism Depositary, the National Institute of Advanced Industrial Science and Technology, Chuo-6, Tsukuba, Ibaraki, Japan.

(4) Mass-scale Culturing
(a) Recovery of Conidiospore

The conidiospore of the transformant (strain #2) obtained via the screening for neoculin-generating strain as described above in (3) was spread on a PD plate using a bamboo skewer, for incubation at 30° C. for 3 to 7 days. 10 ml of 0.01% Tween solution was poured on the plate with the conidiospore growing thereon, to scratch and recover the conidiospore with a sterile dropping pipet (manufactured by Sarstedt).

This was recovered in a 15 ml Falcon, for vigorous agitation for one minute. Then, the cell debris was discarded with sterilized Miracloth. After centrifugation at 4° C. and 4000 rpm for 5 minutes, the supernatant was discarded. 10 ml of 0.01% Tween 80 solution was added to the resulting precipitate, for agitation. After repeating the same procedure once again, the resulting solution was centrifuged at 4° C. and 4000 rpm for 5 minutes, to discard the supernatant. The precipitate was dissolved in 1 ml of sterile water. Several microliters of the recovered solution were diluted to about 10 fold with water, to count the conidiospore using a Thoma counter chamber.

(b) Mass-scale Shaking Culture in DPY Culture Broth (pH 8.0)

120 ml each of the DPY culture broth pH 8.0 was charged in 500 ml flask, and five sets thereof were prepared. The conidiospore was added to the individual flasks to $1 \times 10^7$ cell/liter, for shaking culture at 30° C. and 200 rpm for 72 hours. About 400 ml of culture medium was recovered after cells were discarded with a Miracloth.

(5) Purification of Recombinant Neoculin
(a) Ammonium Sulfate Fractionation

Ammonium sulfate was added to the culture medium recovered from the mass-scale culture described above in (4) to a saturated ammonium sulfate concentration of 60%. Then, the resulting mixture was incubated for 30 minutes. After centrifugation at 10000 rpm and 4° C. for 30 minutes, the resulting precipitate was recovered.

(b) Purification by Phenyl Hydrophobic Column Chromatography

The precipitate resulting from the ammonium sulfate fractionation was dissolved in Buffer A (3 M NaCl, 20 mM Acetate-Na, pH 5.0), for overnight dialysis against Buffer A. After recovery, the solution was passed through a 0.45 μm filter. The resulting filtrate was defined as sample.

Figure 13:
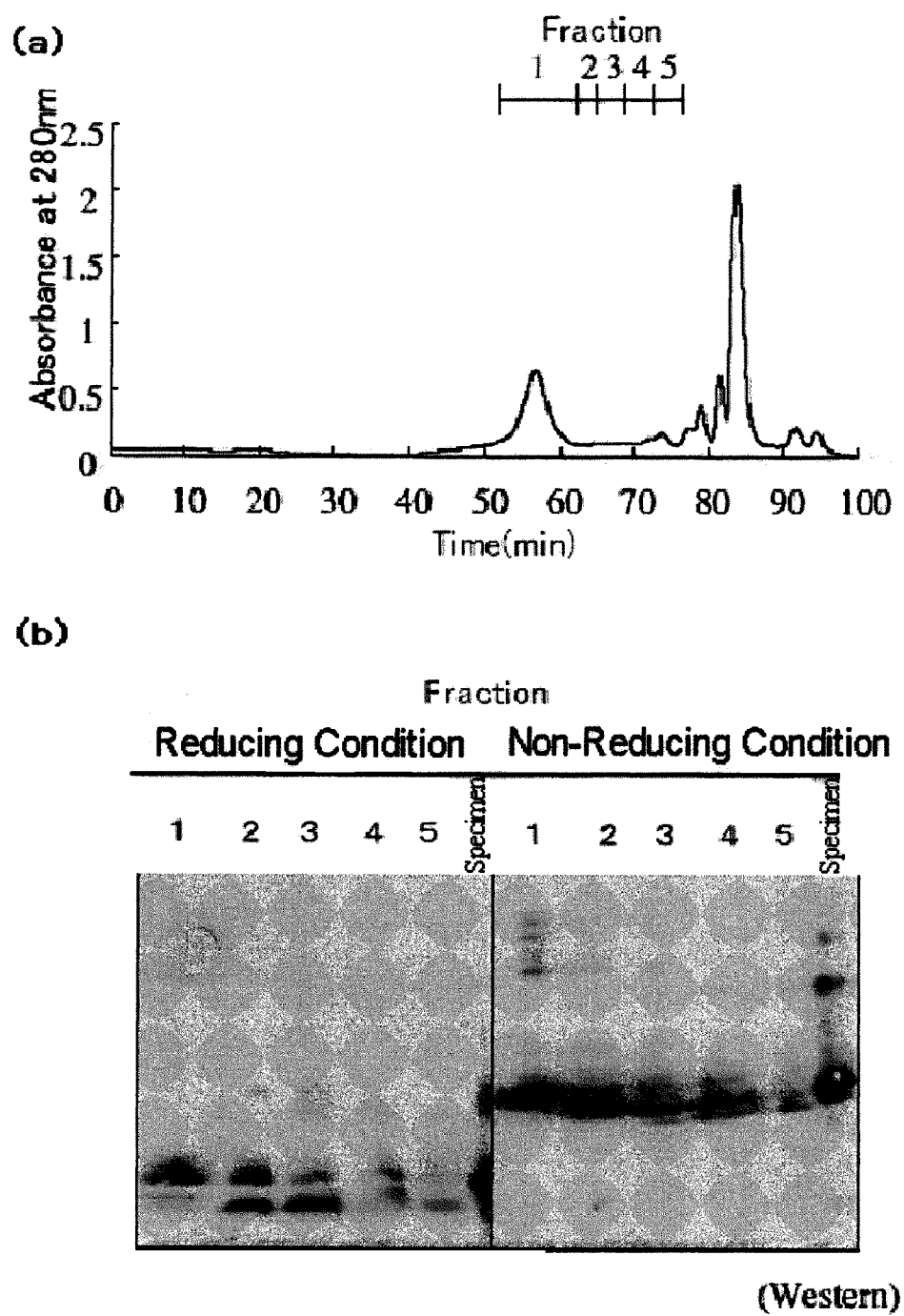
FIG. 13(a) shows an elution pattern after purification by phenyl hydrophobic column chromatography.
FIG. 13(b) shows a chart of the results of western blotting after subjecting the individual fractions to SDS-PAGE under reducing conditions or non-reducing conditions.

As the column, HIC PH-814 (20×150 mm) (manufactured by Shodex) was used. Fractionation was done by phenyl hydrophobic column chromatography using as a mobile phase Buffer A for a 0-20-min period, a 0-100% gradient of Buffer B (20 mM acetate-Na, pH 5.0) in Buffer A for a 20-90 min period, and Buffer B for a 90-110 min period, under a flow condition of 3.0 ml/min (detection; 280 nm) (FIG. 13(a)). After the resulting fractions (Fr. 1-5) were electrophoresed and analyzed by western blotting (FIG. 13 (b)), recombinant neoculin (a heterodimer of NAS and NBS) was eluted in Fr. 1, while a band like the NAS homodimer was mainly observed in Frs. 2-5. Fr. 1 was recovered, for further purification. (FIG. 13).

(c) Purification by Gel Filtration Column Chromatography

The Fr. 1 obtained via purification by phenyl hydrophobic column chromatography was dialyzed against water, freeze-dried and dissolved in a small amount of water. The resulting solution was used as sample.

Figure 14:
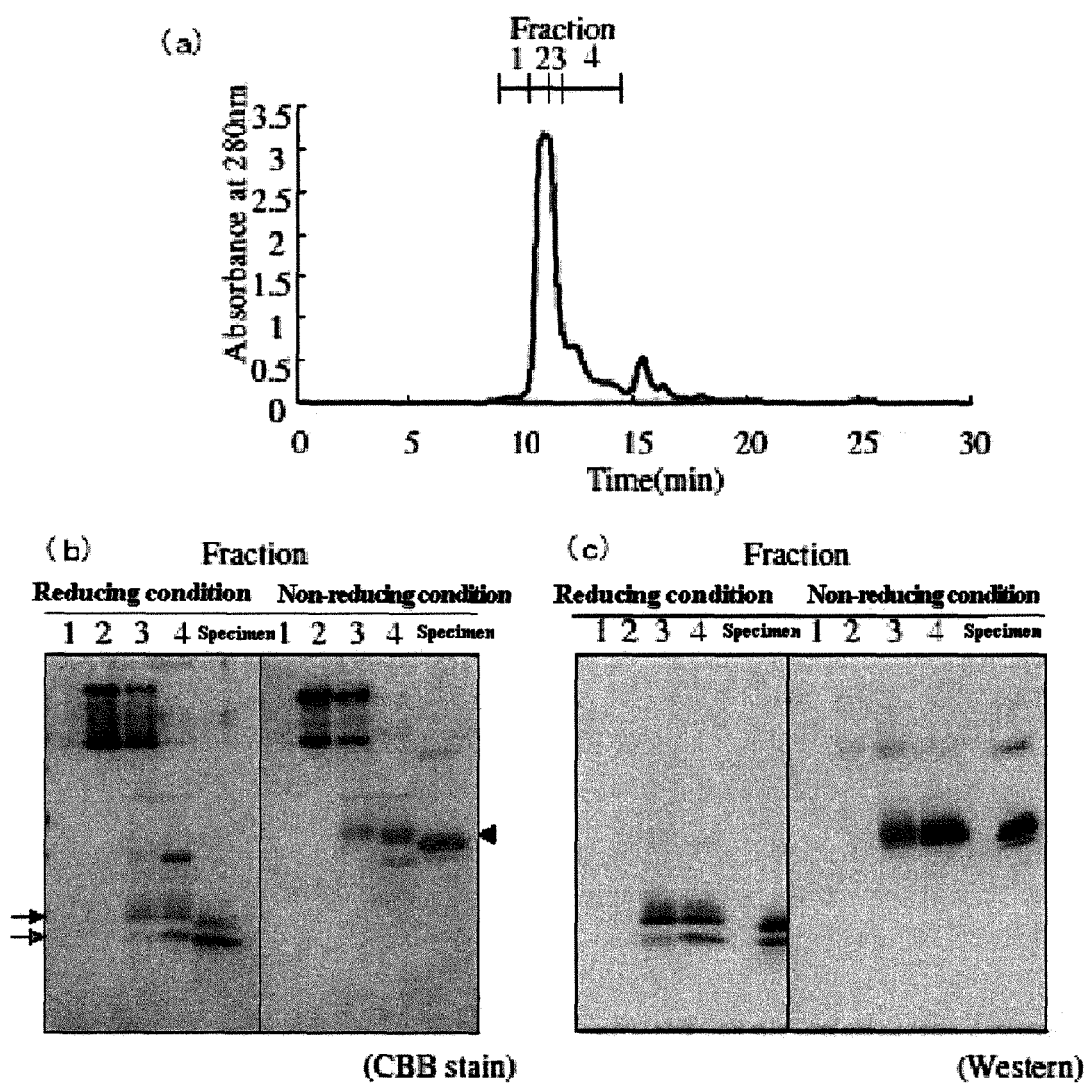
FIG. 14(a) shows an elution pattern of gel filtration column chromatography.
FIG. 14(b) shows a chart of the results of CBB staining after subjecting the individual fractions to SDS-PAGE under reducing conditions or non-reducing conditions.
FIG. 14(c) shows a chart of the analysis of, western blotting after subjecting the individual fractions to SDS-PAGE under reducing conditions or non-reducing conditions.

Using TSK-GEL G3000SW (7.5×300 mm) (manufactured by TOSOH) as the column, fractionation was done by gel filtration column chromatography using 0.5 M NaCl and 50 mM acetate-Na, pH 5.0 as the mobile phase, under a flow condition of 1.0 ml/min (detection; 280 nm) (FIG. 14(a)).

Frs. 1-4 were individually recovered and dialyzed against water, freeze-dried and dissolved in a small amount of water. The solutions were subjected to electrophoresis (SDS-PAGE) under reducing conditions or non-reducing conditions, stained with CBB (FIG. 14(b)) and analyzed by western blotting (FIG. 14(c)). Consequently, it was found that the recombinant neoculin could be eluted in Fr. 3 and Fr. 4.

Among Frs. 1 to 4, a smear band (marked with solid arrow in FIG. 14(b)), which might possibly be NAS, was detected at a position of about 13 kDa in Fr. 3 (lane 3) and Fr. 4 (lane 4) on SDS-PAGE under reducing conditions, while a band (marked with open arrow in FIG. 14(b)), which might possibly be NBS, was detected at a position of about 11 kDa in the Fr. 3 and Fr. 4 on SDS-PAGE under reducing conditions.

By SDS-PAGE under non-reducing conditions, further, a band which might possibly be a heterodimer was detected at a position of about 20 kDa (solid arrowhead in FIG. 14(b)).

Furthermore, Fr. 3 contained a large amount of impure proteins (never detected by western blotting analysis) except neoculin as the intended protein. Alternatively, it was shown that the content of the protein neoculin was very high in Fr. 4.

The amino terminal sequences of the bands at positions of 13 kDa and 11 kDa on SDS-PAGE under reducing conditions in Fr 4 (marked with arrow in lane 4 in the lower left chart in FIG. 14) were analyzed after transfer onto a PVDF film. The protein in the band at the 13 kDa position was Gly-Gly-Gly-Asp-Ser-Val-Leu-Leu-Ser (SEQ ID NO: 19) while the protein in the band at the 11 kDa position was Gly-Gly-Gly-Asp-Asn-Val-Leu-Leu-Ser (SEQ ID NO: 20). These individually correspond to an amino acid sequence of the amino acid residues 1 to 6 in the amino acid sequence shown in SEQ ID NO.2 in the sequence listing and an amino acid sequence of the amino acid residues 1 to 6 in the amino acid sequence shown in SEQ ID NO.6 in the sequence listing, both the sequences following the three Gly residues added to the N terminus so as to enhance the cleavage efficiency with KEX2. Thus, these bands represent NAS and NBS. This indicates that a recombinant neoculin processed individually at accurate positions was obtained.

(6) Verification of Taste-modifying Activity of Recombinant Neoculin

The purified recombinant neoculin was dissolved in water at a concentration of 0.3 mg/ml, to make the evaluation of the taste-modifying activity.

After 200 μl of 0.02N citric acid was given to taste the sourness, 20 μl of the recombinant neoculin solution was tasted and sufficiently touched on tongue. Subsequently, 200 μl of citric acid was again tasted. Sweetness was felt while the sourness was suppressed, so that the taste-modifying activity was confirmed.

This was at a specific activity at almost the same level as that of a specimen (0.3 mg/ml) at the same concentration. 10 minutes after tasting the recombinant neoculin, citric acid was tasted. Even then, the activity was retained. Even when water was drunk, it tasted sweet, and the activity was confirmed to last for 60 minutes.

The aforementioned results show that the vector carrying the DNA of the gene encoding NAS and the vector carrying the DNA of the gene encoding NBS can express neoculin having a taste-modifying activity in the koji mold.

INDUSTRIAL APPLICABILITY

In accordance with the invention, a novel dimer protein neoculin with an excellent taste-modifying activity is provided, which is in a heterodimer structure unlike curculin. Using the protein, a novel taste-modifying composition practically applicable to foods and the like can be provided.

In accordance with the invention, additionally, the amino acid sequences of the subunits constituting the protein are provided. By an appropriate synthetic method following the amino acid sequences, the protein can be provided.

In accordance with the invention, still further, the DNA of the gene encoding the protein is provided, which enables to provide efficiently the protein by selecting an appropriate host, particularly using the koji mold as the host, and with a use of genetic engineering technique.

The invention claimed is:

1. An isolated DNA encoding a Neoculin Acidic Subunit (NAS) polypeptide comprising the amino acid sequence of SEQ ID NO:2.

2. An isolated DNA encoding a Neoculin Acidic Subunit precursor (PNAS) polypeptide comprising the amino acid sequence of SEQ ID NO:3.

3. A recombinant vector comprising the isolated DNA according to claim 1.

4. A recombinant vector comprising the isolated DNA according to claim 2.

* * * * *

SEQUENCE LISTING

<160> NUMBER OF SEQ ID NOS: 20

<210> SEQ ID NO 1
<211> LENGTH: 591
<212> TYPE: DNA
<213> ORGANISM: Curculigo latifolia

<400> SEQUENCE: 1

```
acaatggcgg ccaagtttct tctcaccatt cttgtcacct ttgcggccgt cgctagcctt      60
ggcatggccg acagtgtcct gctctccggg caaactctgt atgccggcca ctccctcacg     120
tcgggcagct ataccttaac catacaaaac aactgcaacc tggtgaaata ccagcacggg     180
aggcagatct gggctagcga cactgacggg cagggctccc aatgccgcct cacattgcgg     240
agtgacggga acctcattat ctacgacgac aacaacatgg tcgtgtgggg gagcgactgc     300
tgggggaaca acggcacgta tgctcttgtt cttcagcagg atggcctctt tgtcatctat     360
ggcccggttt tgtggcccct tggccttaat gggtgccgca gtcttaatgg tgaaatcaca     420
gttgctaagg attctactga accacaacat gaggatatta agatggtgat taataattaa     480
tcaagtgaga ggattgttat gagaataatg agggaatgga agaccaatct catgtcggtg     540
tggcctatct cgacctgttt gcagtgcctt tgttaaaata acacattgct t               591
```

<210> SEQ ID NO 2
<211> LENGTH: 113
<212> TYPE: PRT
<213> ORGANISM: Curculigo latifolia

<400> SEQUENCE: 2

Asp Ser Val Leu Leu Ser Gly Gln Thr Leu Tyr Ala Gly His Ser Leu
1 5 10 15

Thr Ser Gly Ser Tyr Thr Leu Thr Ile Gln Asn Asn Cys Asn Leu Val
20 25 30

Lys Tyr Gln His Gly Arg Gln Ile Trp Ala Ser Asp Thr Asp Gly Gln
35 40 45

Gly Ser Gln Cys Arg Leu Thr Leu Arg Ser Asp Gly Asn Leu Ile Ile
50 55 60

Tyr Asp Asp Asn Asn Met Val Val Trp Gly Ser Asp Cys Trp Gly Asn
65 70 75 80

Asn Gly Thr Tyr Ala Leu Val Leu Gln Gln Asp Gly Leu Phe Val Ile
85 90 95

Tyr Gly Pro Val Leu Trp Pro Leu Gly Leu Asn Gly Cys Arg Ser Leu
100 105 110

Asn

<210> SEQ ID NO 3
<211> LENGTH: 158
<212> TYPE: PRT
<213> ORGANISM: Curculigo latifolia

<400> SEQUENCE: 3

Met Ala Ala Lys Phe Leu Leu Thr Ile Leu Val Thr Phe Ala Ala Val
1 5 10 15

Ala Ser Leu Gly Met Ala Asp Ser Val Leu Leu Ser Gly Gln Thr Leu
20 25 30

Tyr Ala Gly His Ser Leu Thr Ser Gly Ser Tyr Thr Leu Thr Ile Gln
35 40 45

-continued

```
Asn Asn Cys Asn Leu Val Lys Tyr Gln His Gly Arg Gln Ile Trp Ala
 50                  55                  60

Ser Asp Thr Asp Gly Gln Gly Ser Gln Cys Arg Leu Thr Leu Arg Ser
 65                  70                  75                  80

Asp Gly Asn Leu Ile Ile Tyr Asp Asp Asn Met Val Val Trp Gly
                 85                  90                  95

Ser Asp Cys Trp Gly Asn Asn Gly Thr Tyr Ala Leu Val Leu Gln Gln
                100                 105                 110

Asp Gly Leu Phe Val Ile Tyr Gly Pro Val Leu Trp Pro Leu Gly Leu
                115                 120                 125

Asn Gly Cys Arg Ser Leu Asn Gly Glu Ile Thr Val Ala Lys Asp Ser
            130                 135                 140

Thr Glu Pro Gln His Glu Asp Ile Lys Met Val Ile Asn Asn
145                 150                 155

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atggcggcca agtttcttct cac                                              23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taatcaccat cttaatatcc tcatg                                            25

<210> SEQ ID NO 6
<211> LENGTH: 114
<212> TYPE: PRT
<213> ORGANISM: Curculigo latifolia

<400> SEQUENCE: 6

Asp Asn Val Leu Leu Ser Gly Gln Thr Leu His Ala Asp His Ser Leu
 1               5                  10                  15

Gln Ala Gly Ala Tyr Thr Leu Thr Ile Gln Asn Lys Cys Asn Leu Val
                20                  25                  30

Lys Tyr Gln Asn Gly Arg Gln Ile Trp Ala Ser Asn Thr Asp Arg Arg
            35                  40                  45

Gly Ser Gly Cys Arg Leu Thr Leu Leu Ser Asp Gly Asn Leu Val Ile
        50                  55                  60

Tyr Asp His Asn Asn Asn Asp Val Trp Gly Ser Ala Cys Trp Gly Asp
 65                  70                  75                  80

Asn Gly Lys Tyr Ala Leu Val Leu Gln Lys Asp Gly Arg Phe Val Ile
                85                  90                  95

Tyr Gly Pro Val Leu Trp Ser Leu Gly Pro Asn Gly Cys Arg Arg Val
                100                 105                 110

Asn Gly

<210> SEQ ID NO 7
```

```
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggggacaact tgtatagaa aagttgatgc atttcatggt gttttgatca tt            52

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggggactgct tttttgtaca aacttgtcga gctactacag atcttgcta              49

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggggacaagt ttgtacaaaa aagcaggctc taaacgtggg ggggggaca gtgtcctgct   60 ctcc                                                              64

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggggaccact ttgtacaaga aagctgggtt taattaagac tgcggcaccc             50

<210> SEQ ID NO 11
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggacaagt ttgtacaaaa aagcaggctc taaacgtggg ggggggaca gtgtcctgct   60 ctccg                                                             65

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggggaccact ttgtacaaga aagctgggtt tatccaccat taacacggcg             50
```

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
ggggacagct ttcttgtaca aagtgggtga tctgtagtag ctcgtgaa            48

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
ggggacaact ttgtataata aagttggatc ttggatataa aaatccaaat atg       53

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ggggacagct ttcttgtaca aagtgggatc tgtagtagct cgtgaag              47

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ggggacaact ttgtataata aagttgtttc ctataataga ctagcgtgc            49

<210> SEQ ID NO 17
<211> LENGTH: 477
<212> TYPE: DNA
<213> ORGANISM: Curculigo latifolia

<400> SEQUENCE: 17
atggcggcca gtttcttcct caccattctt gtcacctttg cggccgtcgc tagccttggc    60
atggccgaca atgtcctgct ctccgggcaa actctgcatg ccgaccactc tctccaggcg   120
ggcgcctata ccttaaccat acaaaacaag tgcaacctgg tgaaatacca gaacgggagg   180
cagatctggg ctagcaacac tgacaggcgg ggctccggct gccgcctcac attgctgagt   240
gacgggaacc tcgttatcta cgaccacaac aacaacgacg tgggggag cgcctgctgg   300
ggggacaacg gcaagtatgc tcttgttctt cagaaggatg gcagatttgt catctatggc   360
ccggttttgt ggtcccttgg ccctaatggg tgccgccgtg ttaatggtgg aatcacagtt   420
gctaaggatt ctactgaacc acaacatgag gatattaaga tggtgattaa taattaa     477

<210> SEQ ID NO 18
<211> LENGTH: 3481
<212> TYPE: DNA

<213> ORGANISM: Aspergillus nidulans

<400> SEQUENCE: 18

```
gatctgtagt agctcgtgaa gggtggagag tatatgatgg tactgctatt caatctggca      60
ttggacagtg agtttgagtt tgatgtacag ttggagtcgt tactgctgtc atcccttat     120
actcttcgat tgttttcga accctaacgc caagcacgct agtctattat aggaaaggat     180
cctctagagt cgacctgcag gcatgcaagc tggtcagctt ctcttggcaa tagctgcccg     240
tatgacagga agtccgtaag tacttcccct cccacacttc agtatacgtc ccagtatggt     300
gtggctgacg attcgagggc cggcatccct acgtcattag tcaaaattgg atactggtat     360
tgtgcttgag ggcgcggagc cggagagctc agaagatata tccgggttga tctgttctca     420
tattcttttc agattagaat tactgcttcg tacattccct gataattgat atcttccttc     480
aatgacagaa atagatatta aacagaaatg gtaatagtcc cggtgcggag aaatacaccg     540
cccccgcgca ctcgtatata caacagtcaa attcaggagc cacaacatat ctagctcacc     600
gtcactaaga tatggcgtcc gcttagcata ggagtaactg ttttgaagag ataaatgctg     660
ccgatatata tacgtttacg caattgccca tgtgaagtca tgcagagtcg ttacttgaat     720
tcaaatgttc tatagccttc ccaagcactc ttaaccgaag atcccgtctt tatctcgcat     780
caaacaaagg aaataaatcg caaatctcta acgcccaata ttatctacag acgctcaaag     840
tagccctcgc tctcgagcat gaggatgatc tcatggacaa tggaacgaac gctctgcttg     900
gaaacgtcga ccacaaggtt ggcgttggtg ggggcctcgt aggggtcatc gacaccggtg     960
aagcccttga tttcaccgcg gcgggccttg gcgtagatac cgcgcttgtc agtggcctca    1020
cagtattcga ggggagtgtt gacgtgaacc aggaagaaag agccaccggt gctctggaca    1080
gcctcacggg ccgccttgcg ggagtgctcg tagggagcaa tggggggcagc gataacagcg    1140
gcaccggcgc gggtgagttc accggcgacg aaagcgatgc gctggacgtt ggtgtggcgg    1200
tcctcacgac tgaagcccag ctcagaggag agctcgtggc ggacagtgtc accaaggagg    1260
agtgtgacag agcgtccacc ctgctggttg agagtgacct ggagagcacg agcgatggcg    1320
tccttgccgg agttcatgta accggtaagg aagatggtga aaccctggag ggcgcgaggg    1380
gggctagact cgcgcaggat cttgacaact tcggggtaag agaaccactc agggatgtga    1440
gcaccggtac ggagacggtt acggagttca gttccggaga tgtcgagggt cttggtgccc    1500
gcaggaacct cgtccttggg catgtactca tcggtgtcgg ggaggtaggt gacttgctgg    1560
aattcaacga cctcgatacc gagctccgcg cggtacttct cgaccgcgtg ctgagcatcg    1620
taggggccgt agaactcctg acccttggag ttcttaccag gaccggcgtg gtcacggcca    1680
acaatgaagt gggtggcacc gtggttctta cggatgatag cgtgccagac agcctcacgg    1740
ggaccgccca tgcgcatagc aaggggcaag agagcaagag ccgccattcc gttggggtag    1800
cggggaagaa gggcctggta ggcacggaca cgggtgaagt ggtcaatgtc accgggcttg    1860
gtgagaccga cgacagggtg gataaggaca ttagcttggc gggcgcgagc ggcacggacg    1920
gtcaattcac ggtgagctct gtgcataggg tttctgaggt ctgttagcca tgacattcca    1980
gtctcaagtc aagtaaccag aacgaaccgg gtctggaagg cgacaactcg ggtccagccg    2040
agcttgtcga agtgaatacg gagttccgcg ggggtgtcta aaatcgcgtt agatttatct    2100
ttccttgattt atgcaggctc ctgttgtgtt ctcaaacgta cagcggaggc cgacataatc    2160
gtagtggtta agcttgttga ctgcctcgag ctttccaccg atgtagtact cctcgacctt    2220
ggtgttcagg tacttgatgg cggggtgctc tgggtcaccg ccgaagacga gcttggcctc    2280
```

```
cttctccctg gaataagcaa agatgttaga aattgcgcaa tcctcgttta gataaatgcc    2340
acgtccttgg caaatccgca gcgcccgcta gtcccgccat ccggaagacc aagcgaacgc    2400
ggagtaccaa tgacgaggca gttgcccaag gtcatgaaaa caactcactt gtcagggcgg    2460
tagatgtcgt caattgtaag aatagcaagg ttgcggtcgt cacggaagtc acgcagggtg    2520
acacgggagc caggcttaag gccggcctgt tcaatgactg ccttggaagc atccagagta    2580
atgggcatag agaagaggtt gccgtcggca agacgagact cggcgacgac gctagaaaac    2640
ccccaccatt agcaaaattg gcctatttgc gaatatcatt cccgttatgc actattttcg    2700
cggtctgcct ctcgaaagcg aaagcgaccc cgcacaaggt tggatgggct cgattttgag    2760
gggggagggg ctgcataccc gtcgtagtcc ttctggttca tgaaacctgc gccgcgtcag    2820
tatactttgt ctcgaaactt tgaaataaga caatgtgcgt tgaatggaag gagtaaacgt    2880
accctcaaga ggactgaaac caccgttcat gatcaattca agatcgcaca gctggcgctc    2940
agtgagcacg atggagggaa gagtggcggc ctcggcctcg agctggtcgt ggcggggagc    3000
atcgcgagcg atgaggtcct tgaggacacc accgtgagga gtgttagcca tattgaatga    3060
actgtgcttt acaagaatga aaatgatccg gtggaaggag aggaaggtgc ggaagaataa    3120
tggtgatgga gaagtgggaa agctgcgagt tttaaaaaaa cgatggcgca aaagggccgc    3180
aagccaacaa ttgcggaacc agatttaatt caggagaacg attgactgga ttccctgccc    3240
ggaccagcca agtaaactgc cggcctggat tcagagtggg gggctacgtc gtctacgtac    3300
tccatatact aatcctacaa ggttatccag acttcctgct cagagtatca ggtatcatct    3360
atactatcag gtagttcact ccacatatcg agggcgaaac aataaaagtg gaaggtttcg    3420
accaagtacc gtacgaacga gacgaacgag gagccatatt tggatttta tatccaagat    3480 c                                                                  3481

<210> SEQ ID NO 19
<211> LENGTH: 9
<212> TYPE: PRT
<213> ORGANISM: Curculigo latifolia

<400> SEQUENCE: 19

Gly Gly Gly Asp Ser Val Leu Leu Ser
1               5

<210> SEQ ID NO 20
<211> LENGTH: 9
<212> TYPE: PRT
<213> ORGANISM: Curculigo latifolia

<400> SEQUENCE: 20

Gly Gly Gly Asp Asn Val Leu Leu Ser
1               5
```